United States Patent [19]

Bodor

[11] Patent Number: 4,710,495

[45] Date of Patent: Dec. 1, 1987

[54] SOFT STEROIDS HAVING ANTI-INFLAMMATORY ACTIVITY

[75] Inventor: Nicholas S. Bodor, Gainesville, Fla.

[73] Assignee: Otsuka Pharmaceutical Co., Ltd., Tokyo, Japan

[21] Appl. No.: 721,282

[22] Filed: Apr. 8, 1985

Related U.S. Application Data

[63] Continuation-in-part of Ser. No. 626,535, Jun. 29, 1984, abandoned, which is a continuation of Ser. No. 418,458, Sep. 15, 1982, abandoned, which is a continuation-in-part of Ser. No. 265,785, May 21, 1981, abandoned, which is a continuation-in-part of Ser. No. 168,453, Jul. 10, 1980, abandoned.

[51] Int. Cl.$^4$ .................. A61K 31/58; A61K 31/56; C07J 21/00; C07J 1/00
[52] U.S. Cl. ........................ 514/174; 540/36; 540/38; 260/397.45; 514/179; 514/180
[58] Field of Search ............. 260/397.1, 397.4, 397.45; 540/36, 38; 514/174, 179, 180

[56] References Cited

U.S. PATENT DOCUMENTS

| | | | |
|---|---|---|---|
| 3,558,675 | 1/1971 | Sarett et al. | 260/397.4 |
| 3,856,828 | 12/1974 | Phillipps et al. | 260/397.1 |
| 4,093,721 | 6/1978 | Phillipps et al. | 260/397.1 |
| 4,263,289 | 4/1981 | Edwards | 260/397.1 |

Primary Examiner—Leonard Schenkman
Assistant Examiner—Joseph A. Lipovsky
Attorney, Agent, or Firm—Burns, Doane, Swecker & Mathis

[57] ABSTRACT

Novel soft steroid anti-inflammatory agents, said agents being esters or thioesters of 17α-alkoxy-11β-hydroxyandrost-4-en-3-one-17β-carboxylic acids, pharmaceutical compositions containing said agents, novel chemical intermediates useful in the preparation of said agents and methods of administering same to mammals in the treatment of inflammation. Preferred compounds are the haloalkyl esters of 17α-alkoxy-11β-hydroxyandrost-4-en-3-one-17β-carboxylic acids.

70 Claims, No Drawings

SOFT STEROIDS HAVING ANTI-INFLAMMATORY ACTIVITY

CROSS-REFERENCE TO RELATED APPLICATIONS

This application is a continuation-in-part to my earlier copending application Ser. No. 626,535, now abandoned filed June 29, 1984, which was a continuation of my application Ser. No. 418,458, filed Sept. 15, 1982, now abandoned, which was a continuation-in-part of my application Ser. No. 265,785, filed May 21, 1981, now abandoned, which was a continuation-in-part of my application Ser. No. 168,453, filed July 10, 1980, now abandoned. All of said earlier applications are expressly incorporated by reference herein in their entireties and relied upon.

TECHNICAL FIELD OF THE INVENTION

The invention relates to novel soft steroids having anti-inflammatory activity, pharmaceutical compositions containing said soft steroids, novel chemical intermediates useful in the preparation of the steroids, and methods of administering said steroids to mammals in the treatment of inflammation.

BACKGROUND ART

Successful predictions on a rational basis of the biological activity of compounds leading to new drugs are the main objective of drug designers. This has usually been achieved by considering a known bioactive molecule as the basis for structural modifications, either by the group or biofunctional moieties approach or by altering the overall physical-chemical properties of the molecule. Thus, the main aim has been to design, synthesize, and test new compounds structurally analogous to the basic bioactive molecule which have, however, improved therapeutic and/or pharmacokinetic properties. Although "vulnerable" moities have been identified as the ones whose role is the bioinactivation or metabolic elimination of the drug after it has performed its role, little or no attention has been paid in the drug-design process to the rational design of the metabolic disposition of the drugs. This has been the case despite the fact that the toxicity of a number of bioactive molecules is due to their increased elimination half-life, stability, or other factors introduced during the design of increasing their activity. Drugs and particularly their metabolic processes contribute to the various toxic processes by formation of active metabolites. The phenomenon of metabolic activation to macromolecules is the initial step in cell damage. It is also clear that the most toxic metabolites will not survive long enough to be excreted and identified; thus, studies of the stable metabolites may provide misleading information.

It is clear that, in order to prevent and/or reduce toxicity problems related to drugs, the metabolic disposition of the drugs should be considered at an early stage of the drug-design process. This is true particularly when one considers that the body can attack and alter chemically quite stable structures and that, even if a drug is 95% excreted unchanged, the unaccounted small portion can, and most likely will, cause toxicity.

"Soft drugs" can be defined as biologically active chemical compounds (drugs) which might structurally resemble known active drugs (soft analogues) or could be entirely new types of structures, but which are all characterized by a predictable in vivo destruction (metabolism) to nontoxic moieties, after they achieve their therapeutic role. The metabolic disposition of the soft drugs takes place with a *controllable rate* in a predictable manner.

The present inventor has found five major classes of soft drugs. One of the most useful classes was termed the "inactive metabolite" approach which can be advantageously employed to design especially valuable "soft drugs." This approach starts with a known inactive metabolite of a drug or a drug class; followed by modifying the metabolite to resemble structurally (isoteric and/or isoelectronic) the active drug (i.e., activation); and designing the metabolism of the activated species to lead to the starting inactive metabolite after achieving the desired therapeutic role, without the formation of toxic intermediates (i.e., predictable metabolism). The "inactive metabolite" approach further allows controlling the rate of metabolism and pharmacokinetic properties by molecular manipulation in the activation stage. Also, if no useful inactive metabolite is known, one can be designed by the introduction of transporting groups in noncritical structural parts.

SUMMARY OF THE INVENTION

The present inventor has now applied his inactive metabolite approach to the case of the natural and synthetic glucocorticosteroids and has designed the soft steroidal anti-inflammatory agents of the present invention, beginning with the known or analogously designed inactive natural metabolites of the glucocorticosteroids. Thus, for example, in the case of hydrocortisone, one of its major, inactive metabolites, cortienic acid, i.e., $11\beta$, $17\alpha$-dihydroxyandrost-5-en-3-one-$17\beta$-carboxylic acid, has been used as a starting point and activated by the introduction of suitable nontoxic $17\alpha$- and $17\beta$-substituents, which activated derivatives will cleave in vivo, at the $17\beta$-position, and possibly also the $17\alpha$-position, after accomplishment of their nontoxic role, to predetermined or designed inactive metabolites, e.g., non-toxic moieties.

In accord with the foregoing, the present invention provides novel soft steroids having anti-inflammatory activity, said steroids having the structural formula

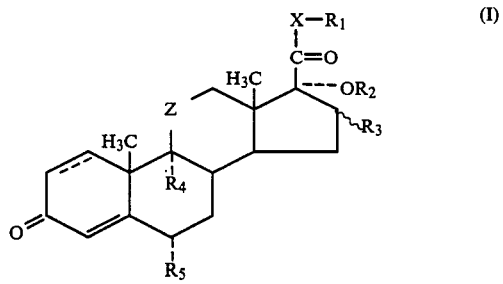

wherein:

$R_1$ is $C_1$-$C_{10}$alkyl; $C_2$-$C_{10}$(monohydroxy or polyhydroxy)alkyl; $C_1$-$C_{10}$ (monohalo or polyhalo)alkyl; or —$CH_2COOR_6$ wherein $R_6$ is unsubstituted or substituted $C_1$-$C_{10}$ alkyl, $C_3$-$C_8$cycloalkyl, $C_3$-$C_8$cycloalkenyl or $C_2$-$C_{10}$alkenyl, the substituents being selected from the group consisting of halo, lower alkoxy, lower alkylthio, lower alkylsulfinyl, lower alkylsulfonyl,

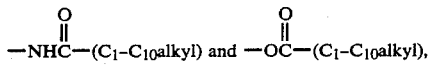

or $R_6$ is unsubstituted or substituted phenyl or benzyl, the substituents being selected from the group consisting of lower alkyl, lower alkoxy, halo, carbamoyl, lower alkoxycarbonyl, lower alkanoyloxy, lower haloalkyl, mono(lower alkyl)amino, di(lower alkyl)amino, mono(lower alkyl)carbamoyl, di(lower alkyl)carbamoyl, lower alkylthio, lower alkylsulfinyl and lower alkylsulfonyl; or $R_1$ is —$CH_2CONR_7R_8$ wherein $R_7$ and $R_8$, which can be the same or different, are each hydrogen, lower alkyl, $C_3$-$C_8$ cycloalkyl, phenyl or benzyl, or $R_7$ and $R_8$ are combined such that —$NR_7R_8$ represents the residue of a saturated monocyclic secondary amine; or $R_1$ is unsubstituted or substituted phenyl or benzyl, the substituents being selected from the group of phenyl and benzyl substituents defined hereinabove with respect to $R_6$; or $R_1$ is

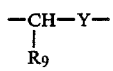

(lower alkyl) wherein Y is —S—, —SO—, —$SO_2$— or —O— and $R_9$ is hydrogen, lower alkyl or phenyl, or $R_9$ and the lower alkyl group adjacent to Y are combined so that $R_1$ is a cyclic system of the type

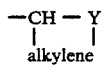

wherein Y is defined as above and the alkylene group contains 3 to 10 carbon atoms, of which at least 3 and no more than 6 are ring atoms; or $R_1$ is

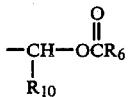

wherein $R_6$ is defined as hereinabove and $R_{10}$ is hydrogen, lower alkyl, phenyl or haloalkyl;

$R_2$ is unsubstituted or substituted $C_1$-$C_{10}$ alkyl, $C_3$-$C_8$ cycloalkyl, $C_3$-$C_8$ cycloalkenyl or $C_2$-$C_{10}$ alkenyl, the substituents being selected from the group consisting of halo, lower alkoxy, lower alkylthio, lower alkylsulfinyl, lower alkylsulfonyl,

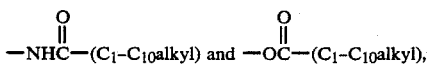

or $R_2$ is unsubstituted or substituted phenyl or benzyl, the substituents being selected from the group consisting of lower alkyl, lower alkoxy, halo, carbamoyl, lower alkoxycarbonyl, lower alkanoyloxy, lower haloalkyl, mono(lower alkyl)amino, di(lower alkyl)amino, mono(lower alkyl)carbamoyl, di(lower alkyl)carbamoyl, lower alkylthio, lower alkylsulfinyl and lower alkylsulfonyl;

$R_3$ is hydrogen, α-hydroxy, β-hydroxy, α-methyl, β-methyl, =$CH_2$, or α- or β-$OR_2$ wherein $R_2$ is identical to $R_2$ as defined hereinabove;

$R_4$ is hydrogen, fluoro or chloro;

$R_5$ is hydrogen, fluoro, chloro or methyl;

X is —O— or —S—;

Z is carbonyl or β-hydroxymethylene;

and the dotted line in ring A indicates that the 1,2-linkage is saturated or unsaturated.

A group of preferred compounds of formula (I) consists of those wherein:

$R_1$ is $C_1$-$C_6$ alkyl; $C_1$-$C_6$ (monohalo or polyhalo)alkyl; —$CH_2COOR_6$ wherein $R_6$ is $C_1$-$C_6$ alkyl; —$CH_2$—Y—($C_1$-$C_6$ alkyl) wherein Y is —S—, —SO—, —$SO_2$— or —O—; or

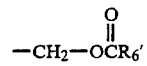

wherein $R_6'$ is $C_1$-$C_6$ alkyl or phenyl;

$R_2$ is $C_1$-$C_6$ alkyl, $C_3$-$C_8$ cycloalkyl, phenyl, benzyl or $C_1$-$C_6$ (monohalo or polyhalo)alkyl;

$R_3$ is hydrogen, α-hydroxy, α-methyl, β-methyl or α-$OR_2$ wherein $R_2$ is identical to $R_2$ as defined hereinabove;

$R_4$ is hydrogen or fluoro;

$R_5$ is hydrogen or fluoro;

Z is β-hydroxymethylene;

and X and the dotted line in ring A are defined as hereinabove.

The invention further provides anti-inflammatory quaternary ammonium salts of selected compounds of formula (I), as discussed in further detail below. Novel intermediates to the compounds of formula (I), e.g., the corresponding compounds wherein $R_1$ is hydrogen, are provided also.

The soft steroids of formula (I) and the quaternary ammonium salts thereof are extremely potent local anti-inflammatory agents; however, by virtue of the fact that their facile in vivo destruction leads only to the inactive steroidal metabolite, the present compounds have far less systemic activity than the known glucocorticosteroids from whose inactive metabolites they are derived. Indeed, many of the compounds of the present invention are entirely devoid of systemic activity. Such minimal—or non-existent—systemic activity means that the compounds of the present invention can be used in the local (e.g., topical) treatment of inflammatory conditions without the serious systemic side effects which attend the use of the known glucocorticosteroids.

DETAILED DESCRIPTION OF THE INVENTION AND THE PREFERRED EMBODIMENTS

With respect to the various groups encompassed by the generic terms used here and throughout this specification, the following definitions and explanations are applicable:

The alkyl, alkenyl and alkylene groupings can be straight or branched-chain groups containing the aforementioned number of carbon atoms. Likewise, the alkyl portions of the alkoxy, alkylthio, alkylsulfinyl, alkylsulfonyl, alkoxycarbonyl, alkanoyloxy, haloalkyl, monoalkylamino, dialkylamino, monoalkylcarbamoyl and dialkylcarbamoyl groupings each can be straight or branched-chain. The term "lower" used in conjunction with any of those groupings or in conjunction with "alkyl" is intended to indicate that each alkyl portion therein can contain 1 to 8 carbon atoms.

Specific examples of alkyl radicals encompassed by formula (I), whether as specific values for $R_1$ or $R_2$, or as a portion of a $R_1$, $R_2$, or $R_3$ group, include methyl, ethyl, propyl, butyl, pentyl, hexyl, heptyl and octyl and their branched-chain isomers, as well as their straight and branched-chain higher homologues in the instances where "alkyl" can contain more than 8 carbon atoms. The alkenyl radicals can be exemplified by vinyl, propenyl and butenyl. Illustrative of the cycloalkyl and cycloalkenyl radicals are cyclopentyl, cyclohexyl, cyclopentenyl and cyclohexenyl. The alkylene moieties are typified by trimethylene, tetramethylene and the like.

The alkoxy, alkylthio, alkylsulfinyl, alkylsulfonyl, alkoxycarbonyl, alkanoyloxy, monoalkylamino, dialkylamino, monoalkylcarbamoyl and dialkylcarbamoyl groupings are of the type

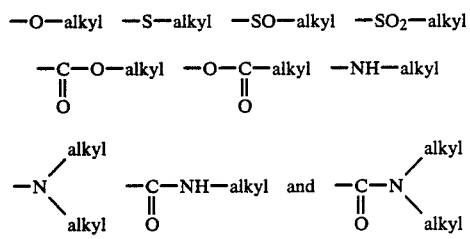

respectively, wherein alkyl is as hereinbefore defined and exemplified.

With respect to the structural variables encompassed by the group of preferred compounds of formula (I) identified hereinabove, the term "$C_1$–$C_6$ alkyl" is used to refer to a straight or branched-chain alkyl group having 1 to 6 carbon atoms, such as methyl, ethyl, n-propyl, isopropyl, n-butyl, isobutyl, sec-butyl, tert-butyl, n-pentyl, n-hexyl and the like. In addition, the term "$C_1$–$C_6$ (monohalo or polyhalo)alkyl" is used to refer to a straight or branched-chain alkyl group having 1 to 6 carbon atoms substituted with from 1 to 3 halogen atoms, the term "halogen" as used herein including a chlorine atom, a bromine atom, an iodine atom or a fluorine atom. Specific examples of the contemplated monohaloalkyl and polyhaloalkyl groups include chloromethyl, dichloromethyl, trichloromethyl, bromomethyl, fluoromethyl, difluoromethyl, trifluoromethyl, 1-fluoroethyl, 1-chloroethyl, 2-chloroethyl, 2,2,2-trichloroethyl, 2,2,2-trifluoroethyl, 1,2-dichloroethyl, 1-chloropropyl, 3-chloropropyl, 1-chlorobutyl, 1-chloropentyl, 1-chlorohexyl, 4-chlorobutyl and the like. Also, the term "$C_3$–$C_8$ cycloalkyl" is used to refer to a cycloalkyl radical having 3 to 8 carbon atoms, such as cyclopropyl, cyclobutyl, cyclopentyl, cyclohexyl, cycloheptyl and cyclooctyl.

When $R_1$ in formula (I) is —$CH_2CONR_7R_8$ wherein —$NR_7R_8$ represents the residue of a saturated monocyclic secondary amine, such monocycles preferably have 5 to 7 ring atoms optionally containing another hetero atom (—O—, —S— or —N—) in addition to the indicated nitrogen atom, and optionally bear one or more substituents such as phenyl, benzyl and methyl. Illustrative of residues of saturated monocyclic secondary amines which are encompassed by the —$NR_7R_8$ term are morpholino, 1-pyrrolidinyl, 4-benzyl-1-piperazinyl, perhydro-1,2,4-oxathiazin-4-yl, 1- or 4-piperazinyl, 4-methyl-1-piperazinyl, piperidino, hexamethyleneimino, 4-phenylpiperidino, 2-methyl-1-pyrazolidinyl, 1- or 2-pyrazolidinyl, 3-methyl-1-imidazolidinyl, 1- or 3-imidazolidinyl, 4-benzylpiperidino and 4-phenyl-1-piperazinyl.

Selected compounds of formula (I), i.e., compounds wherein $R_1$ is α-haloalkyl, readily form the corresponding soft quaternary ammonium salts which are likewise useful as soft anti-inflammatory agents. Thus, for example, the selected haloalkyl derivative of formula (I) can simply be reacted with a tertiary amine

or an unsaturated amine

to afford the corresponding quaternary ammonium salt. The reactants are generally used in approximately equimolecular proportions and the reaction is conducted in the presence of an inert solvent (e.g., ether, acetonitrile, $CH_2Cl_2$, $CH_3NO_2$, dimethylformamide, or the like), at a temperature of from room temperature to the reflux temperature of the solvent, for approximately 2 to 24 hours. Alternatively, the reaction can be conducted in the absence of a solvent by mixing the two reactants together and maintaining them at room temperature or between 20° to 70° C. for 2 to 24 hours. In either case, the crystalline salt formed can be purified by crystallization from an ether-ethanol mixture, or the like.

The expression "unsaturated amine" used above denotes N-heterocyclic unsaturated systems having 3 to 10 members in the ring, and substituted derivatives thereof, where the unsaturation corresponds to the maximum number of non-cumulative double bonds, provided that the nitrogen atom contains no hydrogen atom as a substituent. The following examples will sufficiently illustrate the scope of the defined term:

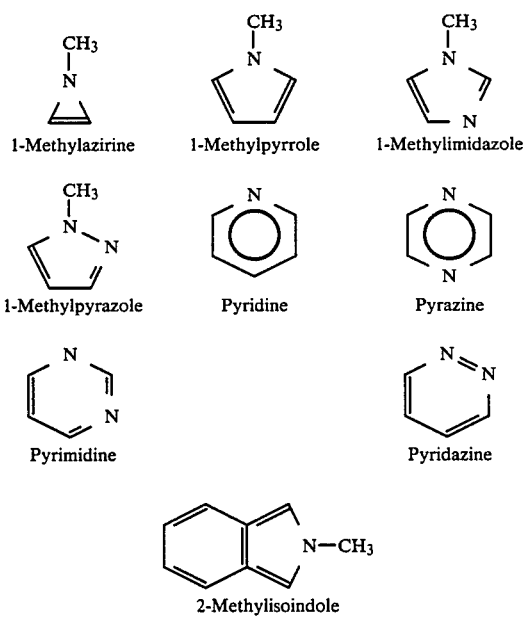

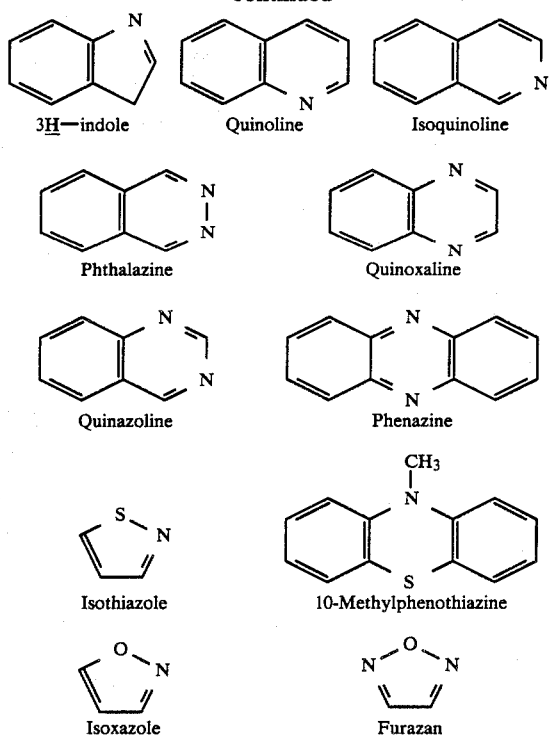

3H—indole  Quinoline  Isoquinoline

Phthalazine  Quinoxaline

Quinazoline  Phenazine

Isothiazole  10-Methylphenothiazine

Isoxazole  Furazan

Substituted derivatives of the unsaturated amines include groups as shown above containing one or more alkyl, —COO(alkyl) or —OCO(alkyl) substituents.

With respect to the expression "tertiary amine," this expression denotes amines wherein the nitrogen atom has no hydrogen atoms attached thereto and which are not among the N-heterocyclic unsaturated systems encompassed by the expression "unsaturated amine" as defined above. Typically, the term "tertiary amine" includes trialkylamines, wherein the alkyl groups, which can be the same or different, each preferably contain 1 to 8 carbon atoms; trialkoxyamines wherein the alkoxy portions each contain 1 to 8 carbon atoms; tertiary saturated cyclic amines such as quinuclidine or substituted quinuclidine (e.g., 3-acetoxyquinuclidine); and N-substituted derivatives of secondary saturated cyclic amines [e.g., an N-substituted derivative of morpholine, pyrrolidine, imidazolidine, pyrazolidine, piperidine or piperazine, wherein the N-substituent can be a group such as $(C_1-C_8)$alkyl], optionally containing additional substituents such as methyl.

Preferred quaternary ammonium salts include those derived from 1,2-dimethylpyrrolidine, 3-acetoxyquinuclidine, 1-methylpyrrolidine, triethylamine and N-methylimidazole. Especially preferred are the quaternary ammonium salts derived from the reaction of the aforesaid amines with compounds of formula (I) wherein Z is β-hydroxymethylene and $R_1$ is chloromethyl, most especially when $R_2$ is lower alkyl.

While all of the compounds encompassed by formula (I) above essentially satisfy the objectives of the present invention, nevertheless certain groups of compounds remain preferred. A "first" group of preferred compounds of formula (I) has been set forth in the Summary of the Invention hereinabove.

Another preferred group of compounds consists of the compounds of formula (I) wherein Z, X, $R_1$ and $R_2$ are defined as hereinabove, and the remainder of the structural variations are identical to those of hydrocortisone (i.e., $R_3$, $R_4$ and $R_5$ are each a hydrogen atom and the 1,2-linkage is saturated) or of prednisolone (i.e., $R_3$, $R_4$ and $R_5$ are each a hydrogen atom and the 1,2-linkage is unsaturated), most especially when $R_1$ and $R_2$ are as defined with respect to the "first" group of preferred compounds set forth hereinabove.

Another preferred group of compounds consists of the 6α- and/or 9α-fluoro and 16α- or 16β-methyl congeners of the compounds indicated in the preceding paragraph. Within this group, the compounds wherein Z, X, $R_1$ and $R_2$ are defined as hereinabove and the remaining structural variables are identical to those of fludrocortisone, betamethasone and dexamethasone are particularly preferred, most especially when $R_1$ and $R_2$ are as defined with respect to the "first" group of preferred compounds set forth hereinabove. Other compounds of particular interest within this group are those wherein Z, X, $R_1$ and $R_2$ are defined as hereinabove and the remaining structural variables are identical to those of triamcinolone, flumethasone, fluprednisolone or paramethasone, particularly when $R_1$ and $R_2$ are as defined with respect to the "first" group of preferred compounds set forth hereinabove. Yet other interesting compounds are those wherein Z, X, $R_1$ and $R_2$ are defined as hereinabove, $R_3$ is $$\alpha\text{-}O\overset{\displaystyle O}{\underset{\displaystyle \|}{C}}R_2,$$

and the remaining structural variables are identical 1 to those of triamcinolone, particularly when $R_1$ and $R_2$ are as defined with respect to the "first" group of preferred compounds set forth hereinabove.

In each of the groups of compounds indicated in the three preceding paragraphs, the compounds wherein X is oxygen are particularly preferred. Most especially preferred are the compounds encompassed by the groups indicated above wherein Z is β-hydroxymethylene, wherein X is oxygen, wherein $R_2$ is $C_1-C_6$ alkyl (particularly methyl, ethyl, propyl or isopropyl), and wherein $R_1$ is $C_1-C_6$ alkyl, $C_1-C_6$ (monohalo)alkyl (particularly chloromethyl) or —$CH_2$—Y—($C_1-C_6$ alkyl) wherein Y is defined as hereinabove (particularly when the $C_1-C_6$ alkyl group is methyl).

The compounds of formula (I) can generally be prepared by known methods, the method of choice being dependent on the identity of the various substituents in the desired final product.

One generally useful method for the preparation of the compounds of formula (I) wherein Z is β-hydroxymethylene and X is oxygen utilizes steroidal starting materials of the formula

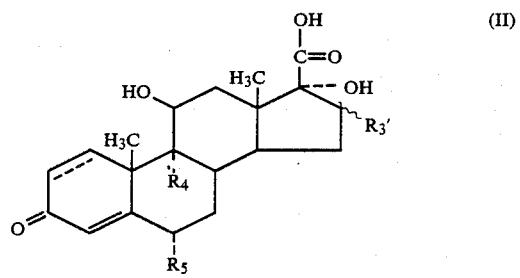

wherein R$_4$ R$_5$ and the dotted line in ring A are defined as before and R$_3'$ is hydrogen, α-methyl, β-methyl, α-OH, β-OH or =CH$_2$ (and which can be conveniently prepared by treatment of the corresponding 21-hydroxypregnenolones of the formula:

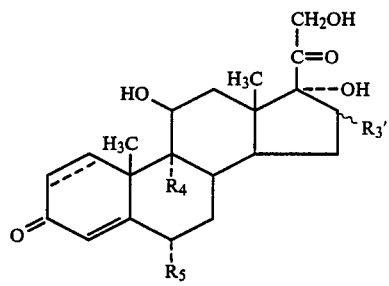

wherein R$_3'$, R$_4$, R$_5$ and the dotted line in ring A are defined as above with NaIO$_4$ in a suitable organic solvent at room or elevated temperature.) According to this process of the invention, a starting material of formula (II) is reacted with R$_2$I and KOH, wherein R$_2$ is defined as above, under anhydrous conditions, in an appropriate inert organic solvent such as dimethylsulfoxide (DMSO), dichloromethane, chloroform or tetrahydrofuran, preferably in the presence of a suitable acid acceptor (e.g., triethylamine, pyridine, calcium carbonate or other appropriate base). Time and temperature are not critical factors; however the reaction is conveniently carried out at a temperature between about 0° C. and room temperature, for about 1 to 6 hours. The resultant novel 17α-alkoxy 17β-carboxylate has the formula:

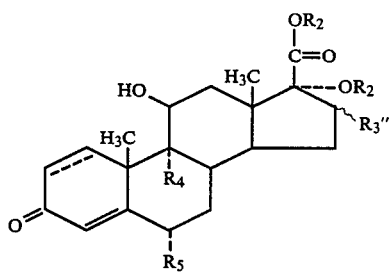

wherein R$_2$, R$_4$, R$_5$ and the dotted line in the A ring are defined as above and R$_3''$ is H, α-CH$_3$, β-CH$_3$, α-OR$_2$, β-OR$_2$ or =CH$_2$. When R$_3''$ in the starting material of formula (II) is α-OH or β-OH, sufficient R$_2$I is generally employed to ensure formation of the alkoxy grouping at the 16-position as well as at the 17-position [i.e., when R$_3'$ in formula (II) is OH, R$_3''$ in the resultant intermediate of formula (III) is α- or β-OR$_2$].

Sometimes, when a compound of formula (I) wherein R$_2$ contains a sulfinyl or sulfonyl grouping is desired, such a grouping is not introduced via the R$_2$I reaction, but is prepared from the corresponding thio-containing R$_2$ derivative at a later stage in the synthetic scheme, as will be discussed in more detail below.

After the above-described introduction of the 17α- and 17β-substituents, the resultant novel steroid of formula (III) is converted to its corresponding 17β-carboxylic acid of the formula:

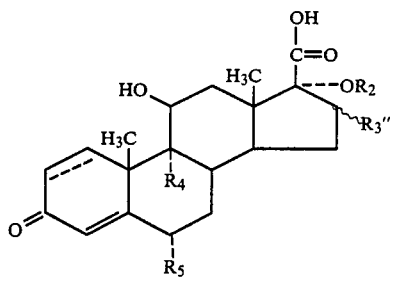

wherein R$_2$, R$_4$, R$_5$ and the dotted line in the A ring are defined as above and R$_3''$ is H. The novel steroid (IV) is typically formed by reacting the steroid of (III) with KOH, under anhydrous conditions, in an appropriate inert organic solvent such as dimethylsulfoxide (DMSO), dichloromethane, chloroform or tetrahydrofuran.

After the above-described preparation of the novel steroid of formula (IV), the formula (IV) is converted to its corresponding metal salt of the formula:

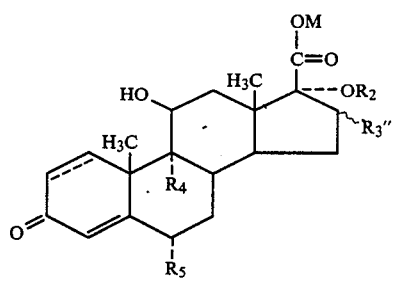

wherein R$_2$, R$_3''$, R$_4$, R$_5$ and the dotted line in the ring A are defined as above, and M is a suitable metal, e.g., alkali metal (such as sodium or potassium), alkaline earth metal/2, or thallium or NH$_4^+$. The novel salt of formula (V) is typically formed by reacting the steroid of formula (IV) with a hydroxide (MOH) or alkoxide (MOR) in an appropriate organic solvent, such as ethyl ether or tetrahydrofuran, at a temperature of 0° C. to room temperature, for 0.5 to 4 hours. Then, the salt of formula (V) is reacted with a compound of the formula R$_1$-W wherein R$_1$ is defined as hereinabove and W is halogen, to afford the desired final product of formula (I). This step of the reaction sequence can be conveniently conducted at room temperature for about 1 to 24 hours, or at the boiling point of the solvent (i.e., acetonitrile, tetrahydrofuran, etc.) When it is desired to introduce a halo-substituted R$_1$ grouping into the steroid, e.g., when a compound of formula (I) wherein R$_1$ is chloromethyl is desired, it has been found that the reaction proceeds well using hexamethylphosphoramide as the solvent at lower temperatures (0°–10° C.) and employing a R$_1$-W reactant wherein W is iodine (e.g., iodochloromethane). When a non-halogen containing R$_1$ grouping is desired (e.g., R$_1$=alkyl or —CH$_2$COOR$_6$ where R$_6$ is alkyl, etc.), no such restrictions need be placed on the R$_1$-W reactant or on the solvent; thus, W can be any halogen, preferably chloro or bromo, and the usual organic solvents such as dimethylformamide, dichloromethane, acetonitrile, tetrahydrofuran or chloroform can, if desired, be used instead of hexamethylphosphoramide. When a compound of formula (I) wherein R$_1$ contains a sulfinyl or sulfonyl grouping is desired, such a grouping is not generally introduced via the $R_1$-W reaction, but is subsequently prepared from the corresponding thio steroid, as described below.

The compounds of formula (I) wherein $R_1$ (or $R_2$) is a sulfinyl- or sulfonyl-containing grouping can be prepared by oxidation of the corresponding thio steroids. Thus, for example, a compound of formula (I) wherein $R_1$ is

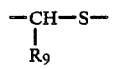

(lower alkyl) [wherein $R_9$ is H, lower alkyl, or combined with the lower alkyl group adjacent to S to form a cyclic system, as described hereinabove] can be reacted with 1 equivalent of m-chloroperoxybenzoic acid at 0°–25° C. for 1 to 24 hours, in a suitable solvent such as chloroform, to afford the corresponding compound of formula (I) wherein $R_1$ is

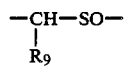

(lower alkyl), or with 2 equivalents of m-chloroperoxybenzoic acid to afford the corresponding compound of formula (I) wherein $R_1$ is

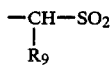

(lower alkyl). This type of reaction can also be utilized to prepare compounds of formula (I) wherein $R_1$ is —$CH_2COOR_6$ wherein $R_6$ is substituted alkyl, cycloalkyl, cycloalkenyl, alkenyl, phenyl, or benzyl, wherein the substituent is lower alkylsulfinyl or lower alkylsulfonyl, from the corresponding lower alkylthio-substituted formula (I) steroids; to prepare compounds of formula (I) wherein $R_1$ is lower alkylsulfinyl- or alkylsulfonyl-substituted phenyl or benzyl from the corresponding lower alkylthio-substituted formula (I) steroids; and to prepare compounds of formula (I) wherein $R_2$ is substituted alkyl, cycloalkyl, cycloalkenyl, alkenyl, phenyl or benzyl wherein the substituent is lower alkylsulfinyl or lower alkylsulfonyl, from the corresponding lower alkylthio-substituted formula (I) steroids.

When the compounds of formula (I) wherein $R_3$ is $\alpha$- or $\beta$-hydroxy are desired, same can be prepared by partial acid hydrolysis of the corresponding compounds of formula (I) wherein $R_3$ is $\alpha$- or $\beta$-$OR_2$, in a suitable solvent medium. Use of a mild reagent, e.g., oxalic acid in methanol, is desirable. Alternatively, hydrolysis of the 16-alkoxy to the 16-hydroxy compound could be carried out at an earlier stage in any synthetic scheme described herein after the introduction of the 16,17$\alpha$-alkoxy, 17$\beta$-carboxylate groupings, e.g., selective hydrolysis of an intermediate of formula (III) having 16 and 17$\alpha$-alkoxy groupings to the corresponding 16-hydroxy 17$\alpha$-alkoxy, followed by a two-step conversion to the corresponding compound of formula (I) as described supra.

Another process for the preparation of the compounds of formula (I) wherein Z is $\beta$-hydroxymethylene and X is oxygen utilizes the same 17$\alpha$-hydroxy-17$\beta$-carboxylic acid starting materials of formula (II) as are employed in the synthetic scheme supra, but involves formation of the 17$\beta$-$COOR_1$ grouping prior to introduction of the 17$\alpha$-$OR_2$ substituent. Essentially, the same non-steroidal reactants, reaction conditions, etc., as described above are used for the introduction of each group. Thus, the starting material of formula (II) is first reacted with KOH in ROH to form the corresponding novel steroid of the formula:

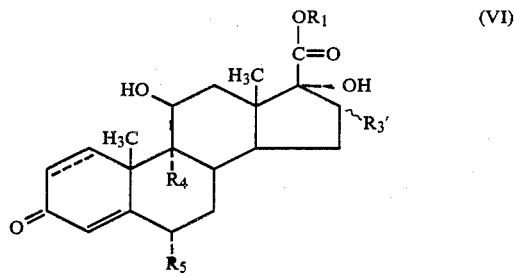

wherein $R_1$, $R_3'$, $R_4$, $R_5$ and the dotted line in ring A are defined as above, which is in turn reacted with $R_2I$ wherein $R_2$ is defined above, to afford the corresponding 17$\alpha$-alkoxy-17$\beta$-carboxylate of formula (I). Thus, again, when the starting material contains a 16-hydroxy group, the 16-alkoxy-17$\beta$-carboxylate of formula (I) will be formed which can then be selectively hydrolyzed, if desired, to the corresponding 16-hydroxy-17$\beta$-carboxylate of formula (I).

After the above-described introduction of the 17$\beta$-carboxylate substituent, the resultant novel steroid of formula (VI) is converted to its corresponding 3-(1',3'-dioxacyclopent-2'-yl) of the formula:

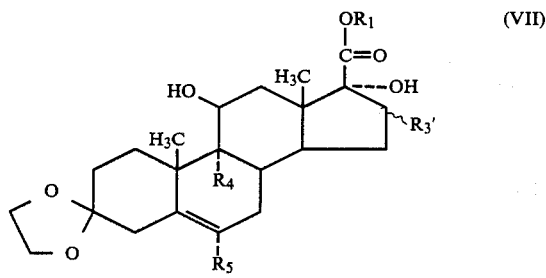

wherein $R_1$, $R_3'$, $R_4$ and $R_5$ and the dotted line are defined as above and $R_3'$ is H. The novel steroid (VII) is typically formed by reacting the steroid of (VI) with ethylene glycol in a solvent such as p-toluenesulfonic acid.

After the above-described introduction of the heterocyclic group at the 3-position, the resultant novel steroid of formula (VII) is converted to its corresponding 17$\alpha$-alkoxy compound of the formula:

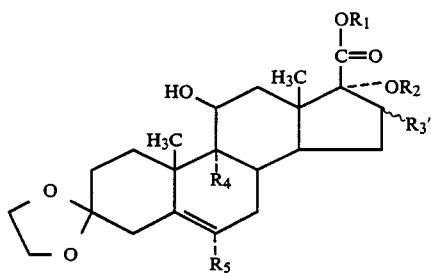

wherein $R_1$, $R_2$, $R_4$, and $R_5$ and the dotted line are defined as above and $R_3'$ is H. The novel steroid (VIII) is typically formed by reacting the steroid of (VII) with KOH, under anhydrous conditions, in an appropriate inert organic solvent such as dimethylsulfoxide, dichloromethane, chloroform or tetrahydrofuran.

After the above-described introduction of the 17α-alkoxy substituent, the resultant novel steroid of formula (VIII) is converted to the corresponding 3-oxo-17β-carboxylic acid of formula (IV) as previously described:

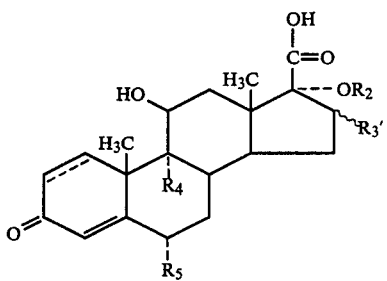

wherein $R_2$, $R_3'$, $R_4$, $R_5$ and the dotted line are defined as above and $R_3'$ is H. The novel steroid of formula (IV) is typically formed by reacting the steroid of formula (VIII) with KOH, under anhydrous conditions, in an appropriate inert organic solvent such as dimethylsulfoxide, dichloromethane, chloroform or tetrahydrofuran. The reaction conditions used to convert III to IV are substantially the same as those used to convert VIII to IV.

After the above-described conversion of the 17β-carboxylate to the 17β-carboxylic acid moiety and conversion of the heterocyclic substituent to the oxo substituent at the 3-position, the resultant novel steroid of formula (IV) is reacted with MOH or MOR to form the corresponding intermediate of the formula (V) as previously described:

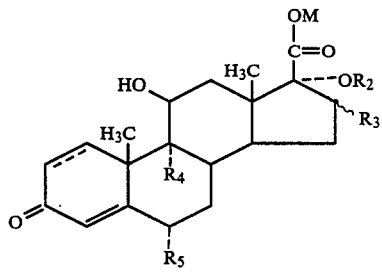

wherein $R_2$, $R_3$, $R_4$, $R_5$ and M and the dotted line in ring A are defined as above, which is then reacted with $R_1W$ wherein $R_1$ and W are defined as above, to afford the corresponding 17β-carboxylate of the formula:

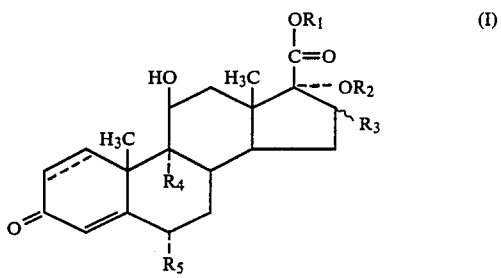

wherein $R_1$, $R_2$, $R_3'$, $R_4$, $R_5$ and the dotted line in ring A are as defined above. Thus, again, when the starting material contains a 16-hydroxy group, the 16-alkoxy-17β-carboxylate of formula (I) will be formed which can then be selectively hydrolyzed, if desired, to the corresponding 16-hydroxy-17β-carboxylate of formula (I). And, again, the compounds of formula (I) in which $R_1$ or $R_2$ is a sulfinyl- or sulfonyl-containing grouping can be conveniently prepared by oxidation of the corresponding thio-containing compounds of formula (I) as detailed hereinabove. Alternatively, the compounds of formula (I) wherein $R_1$ is a sulfinyl- or sulfonyl-containing group [e.g., when $R_1$ is

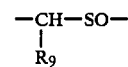

(lower alkyl) or

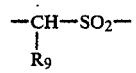

(lower alkyl)] can be prepared by oxidation, preferably with m-chloroperoxybenzoic acid, of the corresponding compounds of formula (I) in which $R_1$ is a thio-containing group.

Other procedures for the preparation of selected compounds of formula (I) will be apparent to those skilled in the art. By way of example, a compound of formula (I) wherein $R_1$ or $R_2$ is halo-substituted can be subjected to a halogen exchange reaction in order to replace the halogen with a different halogen according to the order of reactivity Cl<Br<I. For example, reacting a chloroalkyl 17β-carboxylate of formula (I) with an alkali metal iodide, e.g., sodium iodide, will afford the corresponding iodoalkyl 17β-carboxylate. Similarly, a bromide salt (e.g., lithium bromide) can be reacted with a chloroalkyl 17β-carboxylate to give the corresponding bromoalkyl 17β-carboxylate. A suitable solvent for either reaction may be selected from the group consisting of hexamethylphosphoramide, acetone, ethanol, methyl ethyl ketone, dimethylacetamide, dimethylformamide and acetonitrile.

In like manner, a halogen exchange reaction based on relative solubilities can be used to convert a chloroalkyl 17β-carboxylate or an iodoalkyl 17β-carboxylate of formula (I) to the corresponding fluoroalkyl derivative. Silver fluoride can be employed in this reaction, which is conducted in a suitable organic solvent (e.g., acetonitrile), and which is especially useful in the preparation of the compounds in which $R_1$ is fluoromethyl or fluoroethyl.

The 21-hydroxypregnenolones from which the steroidal starting materials of formula (II) are prepared can be obtained commercially or prepared by known methods. Likewise, the nonsteroidal starting materials used in the various processes discussed above are commercially available or can be prepared by known chemical procedures.

In yet another aspect, the present invention provides novel compounds of the formula:

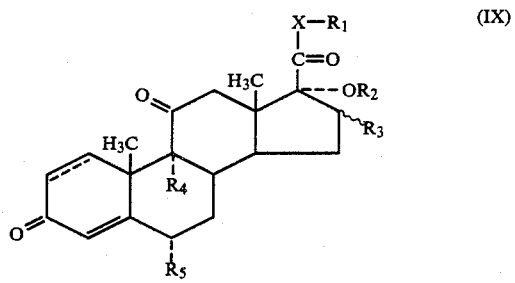

(IX)

wherein $R_1$, $R_2$, $R_3$, $R_4$, $R_5$, X and the dotted line in ring A are as defined with respect to formula (I) above. The 11-keto compounds of formula (IX) can be prepared by the procedures described hereinabove for the preparation of the corresponding 11$\beta$-hydroxy compounds of formula (I). Thus, a starting material corresponding to formula (II) but having an 11-keto group is reacted with $R_2I$, to afford the corresponding novel intermediate corresponding to formula (III) but having an 11-keto group; that intermediate is then converted to the corresponding novel intermediate corresponding to formula (IV); that intermediate is then converted to its metal salt, which corresponds to formula (V) except for the presence of an 11-keto instead of an 11$\beta$-hydroxy group; and the metal salt is then reacted with $R_1W$ to afford corresponding compound of formula (IX). All reaction conditions are as previously described with respect to the corresponding processes for preparing the corresponding compounds of formula (I). Also, the preparation of the compounds of formula (IX), wherein $R_1$ is a sulfinyl- or sulfonyl- containing grouping or wherein $R_3$ is hydroxy generally proceeds as a final step in the synthetic scheme in a manner analogous to that used for the corresponding compounds of formula (I). Further, all of the above-described alternative processes for the preparation of the compounds of formula (I) are equally applicable to the preparation of the compounds of formula (IX) by simply substituting the 11-oxo starting material for the corresponding 11$\beta$-hydroxy steroids used therein, e.g., replacing the 11-hydroxy group in formulas (VI), (VII) and (VIII) with an 11-oxo group and otherwise proceeding as described hereinabove for the reactions (II)→(VI)→(VII)→(VIII)→(IV)→(V)-→(I).

Also, the compounds of formula (IX) can be prepared by reacting the corresponding compounds of formula (I) with an oxidizing agent. The oxidation of a compound of formula (I) in order to convert it into the corresponding compound of formula (IX) is usually carried out by using an oxidizing agent in an appropriate solvent. The solvent may be any conventional solvent, for example, water, an organic acid (e.g. formic acid, acetic acid, trifluoroacetic acid), an alcohol (e.g. methanol, ethanol), a halogenated hydrocarbon (e.g. chloroform, dichloromethane), or the like. The oxidizing agent may also be any conventional agent which is effective for oxidizing a hydroxy group to a carbonyl group, for example, pyridinium chlorochromate, chromium trioxide in pyridine, hydrogen peroxide, dichromic acid, dichromates (e.g. sodium dichromate, potassium dichromate), permanganic acid, permanganates (e.g. sodium permanganate, potassium permanganate), or the like. The oxidizing agent is usually used in an amount of 1 mole or more, preferably 1 to 3 moles, per mole of the compound of formula (I). The reaction is usually carried out at a temperature of 0° to 40° C., preferably at about room temperature, for about 6 to 30 hours.

The novel compounds of formula (IX) are useful as soft steroidal anti-inflammatory agents and also in vivo or in vitro precursors of the corresponding 11$\beta$-hydroxy compounds. Thus, the compounds of formula (IX) can be reduced in vitro to afford the corresponding compounds of formula (I), using a reducing agent known to be capable of reducing the 11-oxo group to an 11$\beta$-hydroxy group without modifying the remainder of the steroidal starting material. Typically, microbiological reduction is advantageous for carrying out the desired conversion, although chemical reduction also is possible. Further, the compounds of formula (IX) may be formulated into appropriate dosage forms (e.g., retention enemas) for the treatment of conditions such as ulcerative colitis. In such dosage forms, it is thought that the compounds of formula (IX) are microbiologically reduced by bacteria in the body (e.g. in the colon) to the highly active 11$\beta$-hydroxy steroids, which elicit the desired anti-inflammatory response.

The preferred compounds of formula (IX) are those which are precursors of the preferred compounds of formula (I) wherein Z is $\beta$-hydroxymethylene, namely corresponding 11-keto compounds of formula (IX). An especially preferred group of compounds of formula (IX) consists of those wherein X, $R_1$ and $R_2$ are defined as above with respect to formula (I) and the remaining structural variations are identical to those of cortisone (i.e. $R_3$, $R_4$ and $R_5$ are each a hydrogen atom and the 1,2-linkage is saturated), of prednisone (i.e. $R_3$, $R_4$ and $R_5$ are each hydrogen and the 1,2-linkage is unsaturated), or of the 6$\alpha$- and/or 9$\alpha$-fluoro and the 16$\alpha$- or 16$\beta$-methyl congeners thereof, particularly when $R_1$ and $R_2$ are as defined with respect to the "first" group of preferred compounds set forth hereinabove. Most especially preferred of these derivatives are those wherein X is oxygen, $R_2$ is $C_1-C_6$ alkyl and $R_1$ is $C_1-C_6$ alkyl, $C_1-C_6$ (monohalo)alkyl [particularly chloromethyl] or —$CH_2$—Y—($C_1$–$C_6$alkyl) [particularly —$CH_2$—Y—$CH_3$].

Under oxidation conditions, it is important to protect the 11-hydroxy group when preparing the compounds of the present invention since it is known that the mixture of dimethylsulfoxide and acetic anhydride has oxidative properties with respect to primary and secondary alcohols. Therefore, it is possible to prepare a 17$\beta$-methylthiomethyl ether derivative having the formula

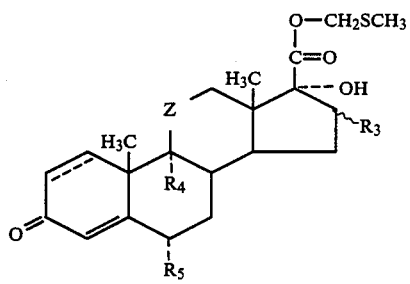

(X)

wherein $R_3$, $R_4$, $R_5$, Z and the dotted line in ring A are as previously defined, from the compound of formula (I) using triethylamine and chloromethylmethylsulfide (ClCH$_2$SCH$_3$). The methylthiomethyl ester of formula (X) is then treated with trifluoroacetic anhydride and pyridine at about $-15°$ C. to give mainly the desired 11$\beta$-trifluoroacetate derivative having the formula

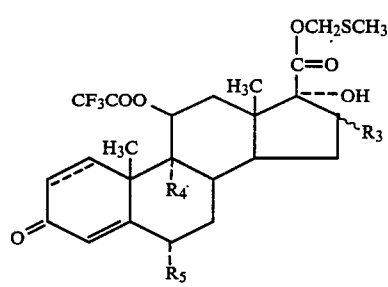

(XI)

wherein $R_3$, $R_4$, $R_5$ and the dotted line in ring A are as previously defined. The 11$\beta$-trifluoroacetate of formula (XI) is then transformed to the 17$\alpha$-methylthiomethyl ester of formula (XII) using dimethyl sulfoxide and acetic anhydride under the same conditions as previously described.

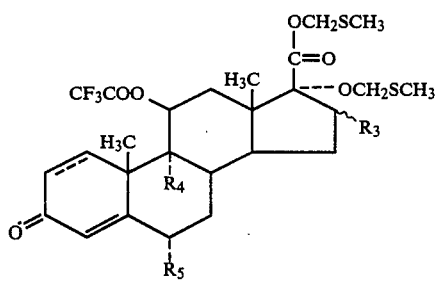

(XII)

wherein $R_3$, $R_4$, $R_5$ and the dotted line in ring A are as previously defined.

The compound of formula (XII) is then reacted with triethylamine and methanol in a sodium bicarbonate and water solution to form a compound having the formula

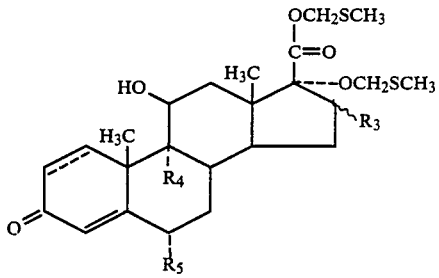

(XIII)

wherein $R_3$, $R_4$, $R_5$ and the dotted line in ring A are as previously defined.

Dexamethasone-type compounds having the structure:

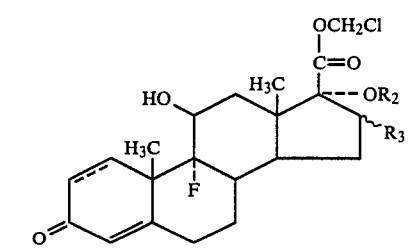

(XIV)

may be prepared in a manner well-known to those of average skill in the art. For instance, a suitable starting material may be

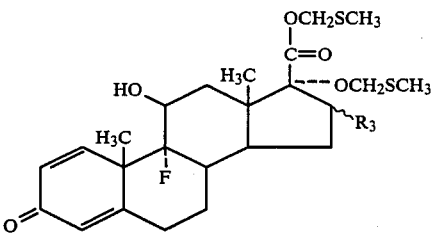

(XIII)

wherein $R_3$ is as previously defined. The compound of formula (XIII) is reacted with KOH in methanol and the potassium salt of tertiary butyl hydroxide in tetrahydrofuran. The novel steroid formed has the formula:

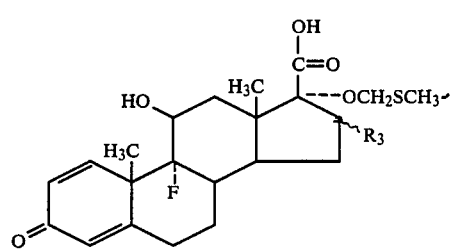

(XV)

wherein $R_3$ is as previously defined. The resultant novel steroid of formula (XV) is then converted to its corresponding chloromethyl ester of the formula:

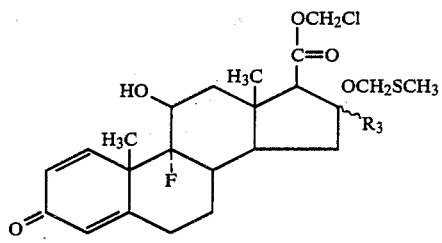

(XIV)

wherein R₃ is as previously defined. The novel steroid (XIV) is typically formed by reacting the steroid of (XV) with KOH and chloromethylmethyl chlorosulfate (ClCH₂SO₂Cl) under phase transfer conditions. the article "Chlorosulfates as Reagants in the Syntheis of Carboxylic Acid Esters Under Phase-Transfer Conditions" by Binderup E. and Hansen E. T., in *Synthetic Communications*, 14(9), 857–864 (1984) discloses the use of chloromethyl chlorosulfate in the synthesis of chloromethyl esters of sensitive carboxylic acids under phase transfer conditions, which synthesis is applicable hereto.

The results of various activity studies of representative species of the invention, discussed in detail below, clearly indicate the potent anti-inflammatory activity and the minimal systemic activity toxicity of the soft steroids of formula (I). In view of this desirable separation of local and systemic activities, the compounds of the invention can be used in the treatment of topical or other localized inflammatory conditions without causing the serious systemic side effects typically exhibited by the known natural and synthetic glucocorticosteroids such as cortisone, hydrocortisone, hydrocortisone, 17α-butyrate, betamethasone 17-valerate, triamcinolone, betamethasone dipropionate and the like.

TOPICAL VASOCONSTRICTION TEST

A topical vasoconstriction test was conducted using the general method of McKenzie, A. W. and R. B. Stoughton, *Arch. Dermatol*, 86, (1962), 608–10. The topical vasoconstriction test was done in order to evaluate the anti-inflammatory potency of the novel compounds of the present invention. A 0.03 M solution of the test compound in acetone/isopropylmyristate 90:10 volume/volume was prepared. An aliquot of 0.05 milliliter was applied to a circular patch, one centimeter in diameter, which was in turn applied against the skin of the flexor surface of the forearm (previously cleansed with ethanol 95% and dried). This application was occluded with a water-impervious film. The patch was removed after about six hours and the blanching score was evaluated one hour later. Two control compounds were used at the same time and under the same conditions. The control compounds were hydrocortisone 17-valerate and cortienic acid 17-ethylcarbonate chloromethylester. The experiment was made in duplicate and the average estimation values for the blanching activity are reported in Table I. The left column of Table I indicates the 17α-substituent of the structure:

TABLE I
BLANCHING STUDIES

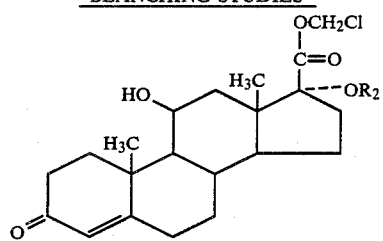

| 17α-substituent | Value |
|---|---|
| —OCH₃* | — |
| —OCH₂H₅** | 0.75 |
| —OC₃H₇** | 1** |
| —OC₄H₉ | 0.5 |
| valerate | 1.5 |
| carbonate | 1.75 |

*The 17-methoxy homologue was determined in a previous study to have low activity.
**Simple study - duplicate experiment not conducted.

The compounds of formula (I) can be combined with suitable non-toxic pharmaceutically acceptable carriers to provide pharmaceutical compositions for use in the treatment of topical or other localized inflammation. Obviously, in view of their lack of systemic activity, the compounds of the present invention are not intended for treatment of conditions where systemic adrenocortical therapy is indicated, e.g., adrenocortical insufficiency. As examples of inflammatory conditions which can be treated with pharmaceutical compositions containing at least one compound of the invention and one or more pharmaceutical carriers, the following can be mentioned: dermatological disorders such as atopic dermatitis, acne, psoriasis or contact dermatitis; allergic states such as bronchial asthma; ophthalmic and otic diseases involving acute and chronic allergic and inflammatory reactions; respiratory diseases; ulcerative colitis; and anorectal inflammation, pruritus and pain associated with hemorrhoids, proctitis, cryptitis, fissures, postoperative pain and pruritus ani. Such compositions may also be applied locally as a prophylactic measure against the inflammation and tissue rejection which arise in connection with transplants.

Obviously, the choice of carrier(s) and dosage forms will vary with the particular condition for which the composition is to be administered.

Examples of various types of preparations for topical/local administration include ointments, lotions, creams, powders, drops, (e.g. eye or ear drops), sprays, (e.g. for the nose or throat), suppositories, retention enemas, chewable or suckable tablets or pellets (e.g. for the treatment of aphthous ulcers) and aerosols. Ointments and creams may, for example, be formulated with an aqueous or oily base with the addition of suitable thickening and/or gelling agents and/or glycols. Such base may thus, for example, include water and/or an oil such as liquid paraffin or a vegetable oil such as arachis oil or castor oil, or a glycolic solvent such as propylene glycol or 1,3-butanediol. Thickening agents which may be used according to the nature of the base include soft paraffin, aluminum stearate, cetostearyl alcohol, polyethylene glycols, woolfat, hydrogenated lanolin and beeswax and/or glyceryl monostearate and/or nonionic emulsifying agents.

The solubility of the steroid in the ointment or cream may be enhanced by incorporation of an aromatic alcohol such as benzyl alcohol, phenylethyl alcohol or phenoxyethyl alcohol.

Lotions may be formulated with an aqueous or oily base and will in general also include one or more of the following, namely, emulsifying agents, dispersing agents, suspending agents, thickening agents, solvents, coloring agents and perfumes. Powders may be formed with the aid of any suitable base, e.g. talc, lactose or starch. Drops may be formulated with an aqueous base also comprising one or more dispersing agents, suspending agents or solubilizing agents, etc. Spray compositions may, for example, be formulated as aerosols with the use of a suitable propellant, e.g, dichlorodifluoromethane or trichlorofluoromethane.

The proportion of active ingredient in the compositions according to the invention will vary with the precise compound used, the type of formulation prepared and the particular condition for which the composition is to be administered. The formulation will generally contain from about 0.0001 to about 5.0% by weight of the compound of formula (I). Topical preparations will generally contain 0.0001 to 2.5%, preferably 0.01 to 0.5%, and will be administered once daily, or as needed. Also, generally speaking, the compounds of the invention can be incorporated into topical and other local compositions formulated substantially as are such presently available types of compositions containing known glucocorticosteroids, at approximately the same (or in the case of the most potent compounds of the invention, at proportionately lower) dosage levels as compared to known highly active agents such as methyl prednisolone acetate and beclomethasone dipropionate or at considerably lower dosage levels as compared to less active known agents such as hydrocortisone.

Thus, for example, an inhalation formulation suitable for use in the treatment of asthma can be prepared as a metered dose aerosol unit containing a representative species of the invention such as chloromethyl 17α-methoxy-11β-hydroxyandrost-4-en-3-one-17β-carboxylate, according to procedures well-known to those skilled in the art pf pharmaceutical formulations. Such an aerosol unit may contain a microcrystalline suspension of the aforementioned compound in suitable propellants (e.g., trichlorofluoromethane and dichlorodifluoromethane), with oleic acid or other suitable dispersing agent. Each unit typically contains 10 milligrams of the aforesaid active ingredient, approximately 50 micrograms of which are released at each actuation. When one of the more potent species of the invention, e.g. chloromethyl 17α-methoxy-9α-fluoro-11β-hydroxy-16α-methylandrosta-1,4-dien-3-one-17β-carboxylate, is employed, each unit typically contains 1 milligram of the active ingredient and releases approximately 5 micrograms at each actuation.

Another example of a pharmaceutical composition according to the invention is a foam suitable for treatment of a wide variety of inflammatory anorectal disorders, to be applied anally or perianally, comprising 0.1% of a compound of formula (I) such as chloromethyl 17α-ethoxy-11β-hydroxyandrost-4-en-3-one 17β-carboxylate, and 1% of a local anaesthetic such as pramoxine hydrochloride, in a mucoadhesive foam base of propylene glycol, ethoxylated stearyl alcohol, polyoxyethylene-10-stearyl ether, cetyl alcohol, methyl paraben, propyl paraben, triethanolamine, and water, with inert propellants. When a more potent compound of the invention is employed, a less active ingredient generally is used, e.g. 0.05% of chloromethyl 9α-fluoro-11β-hydroxy-17α-methoxy-16α-methylandrosta-1,4-dien-3-one-17β-carboxylate.

Yet another pharmaceutical formulation according to the invention is a solution or suspension suitable for use as a retention enema, a single dose of which typically contains 40 milligrams of a compound of the invention such as chloromethyl 17α-ethoxy-11β-hydroxyandrost-4-en-3-one-17β-carboxylate (or 20 milligrams of a more potent compound of the invention such as chloromethyl 9α-fluoro-11β-hydroxy-17α-isopropoxy-16β-methylandrosta-1,4-dien-3-one-17β-carboxylate or chloromethyl 9α-fluoro-11β-hydroxy-16α-methyl-17α-propoxy androsta-1,4-dien-3-one-17β-carboxylate) together with sodium chloride, polysorbate 80 and from 1 to 6 ounces of water (the water being added shortly before use). The suspension can be administered as a retention enema or by continuous drip several times weekly in the treatment of ulcerative colitis.

Other pharmaceutical formulations according to the invention are illustrated in the examples which follow.

Without further elaboration, it is believed that one of ordinary skill in the art can, using the preceding description, utilize the present invention to its fullest extent. Therefore, the following examples are to be construed as merely illustrative and not limitative of the remainder of the specification and claims in any way whatsoever.

EXAMPLE 1

To a solution of hydrocortisone (15 grams, 0.04 mol) in 120 milliliters of tetrahydrofuran and 30 milliliters of methanol at room temperature is added a warm (approximately 50° C.) solution of sodium metaperiodate (25.7 grams, 0.12 mol) in 100 milliliters of water. The reaction mixture is stirred at room temperature for 2 hours, then is concentrated under reduced pressure to remove the tetrahydrofuran and methanol. The solid is triturated with 50 milliliters of water, separated by filtration, washed with water and dried in vacuo at 50° C. for 3 hours. The product, 11β,17α-dihydroxyandrost-4-en-3-one 17β-carboxylic acid (i.e., cortienic acid), melts at 231°-234° C., is obtained in approximately 96% yield (13.76 grams), and can be represented by the structural formula

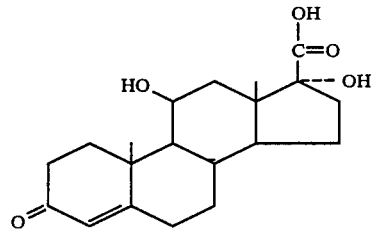

EXAMPLE 2

To a solution of powdered potassium hydroxide (2.14 grams) in dimethylsulfoxide (10 milliliters) was added 11β,17α-dihydroxyandrost-4-en-3-one-17β-carboxylic acid (1.7 gram; 4.88 millimoles). The mixture was stirred for five minutes and immediately followed by addition of methyliodide (1.22 milliliters; 19.5 millimoles). After stirring for one hour and fifteen minutes at 25° C., the mixture was diluted with 100 ml of ethylacetate. The mixture was then washed successively with 10 milliliters water, 10 milliliters Na₂S₂O₃(5% weight- /volume), 10 milliliters NaHCO3 (5% weight/volume) and then three additional times with 10 milliliters water. The organic solution was then dried over MgSO4 and evaporated under partial pressure. The white crystalline crude product weighed 1.73 gram (94% theoretical) and had a melting point of 195° C. to 201° C. Crystallization from CH2Cl2/Pentane raised the melting point to 215° C. to 217° C. then 217° C. to 218.5° C. Elemental analysis: Required C70.18; H8.57; Found C70.16; H8.62. I.R. (KBr) 3500, 1725, 1655, 1210, CM$^{-2}$, H nmr (CDCl3): 0.93 (S,3,18C$\underline{H}$3); 1.43 (S,3,19C$\underline{H}$3); 3.10 (S,3,17OC$\underline{H}$3); 5:65 (S,1,$\overline{C}$=$\overline{CH}$). The product, methyl 11β-hydroxy-17α-methoxyandrost-4-en-3-one-17β-carboxylate, can be represented by the structural formula:

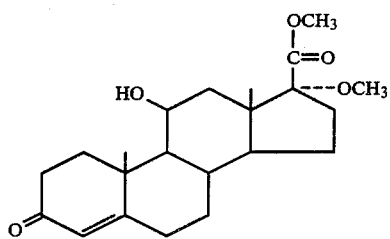

EXAMPLE 3

The methyl 11β-hydroxy-17α-methoxyandrost-4-en-3-one-17β-carboxylate (3.76 grams; 10 millimoles) were stirred overnight (16 hours) at 50° C., under nitrogen in a mixture of powdered potassium hydroxide (4.50 grams) in 15 milliliters dimethylsulfoxide. The reaction mixture was then diluted with 200 milliliters water, acidified with dilute HCl, stirred 30 minutes and extracted with several portions of ethylacetate. The organic layer was then washed with 30 milliliters water, evaporated and taken up into 150 milliliters NaHCO3 solution (5% weight/volume). The aqueous solution was then washed with 30 milliliters methylene chloride, acidified with diluted HCl, filtered, and the residue was dried in vacuo at 40° C. overnight. The crude, yellow, pseudocrystalline product, 11β-hydroxy-17α-methoxyandrost-4-en-3-one-17β-carboxylic acid, weighed 3.05 grams (84% theoretical) $^1$H nmr (DMSOd6): 0.92 (S,3,18C$\underline{H}$3); 1.38 (S,3,19C$\underline{H}$3); 3.04 (S,3,OC$\underline{H}$3); 5.50 (S,1,C=$\overline{CH}$); 8.28 (S,<1,CO$\overline{O}$H). The product can be represented by the structural formula

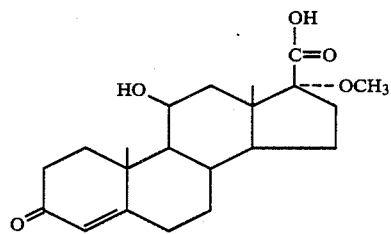

EXAMPLE 4

A 1 normal solution of KOH (3.62 milligrams; 1 millimole) in methanol was added dropwise to the 11β-hydroxy-17α-methoxyandrost-4-en-3-one-17β-carboxylic acid at 0° C. in an ice bath. The solution was evaporated under vacuo and dried thoroughly. The resulting potassium salt was mixed with 10 milliliters dimethylsulfoxide and 4 millimoles chloroiodomethane. After stirring for seven hours at room temperature (24° C.), the mixture contained a precipitate of potassium iodide. The mixture was then diluted with 100 milliliters ethylacetate and washed successively with 18 milliliters water, 10 milliliters Na2S2O3 (5% weight/volume), 10 milliliters NaHCO3 and three times with 10 milliliters water. The product was dried over MgSO4 and evaporated under partial pressure. The dried product was purified by column chromatography from 12 grams of Silica gel (100-200 mesh type 60A special), eluted with EtOAc/CHCl3 20:80 and crystallized from ethylacetate/ether to give a final product that melted at 195° C.-196° C. and $^1$H nmr (CDCl3): 0.95 (S,3,18C$\underline{H}$3); 1.43 (S,3,19C$\underline{H}$3) 3.12 (S,3,OC$\underline{H}$3); 5.60 (S,1,C=$\overline{CH}$); 5.75 (S,2,COOC$\underline{H}$2Cl). IR (KBr): 3400, 1755, 1655, 1205, 1110 (ether) cm$^{-1}$. Elemental analysis: Required: C64.30; H760; C18.63; Found: C64.16; H7.63; C18.63. The product, chloromethyl 11β-hydroxy-17α-methoxyandrost-4-en-3-one-17β-carboxylate, can be represented by the structural formula:

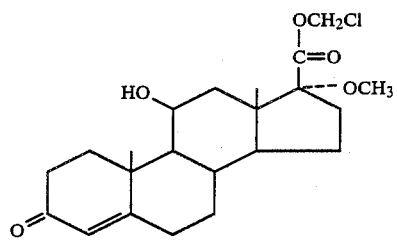

EXAMPLE 5

11β,17α-Dihydroxyandrost-4-en-3-one-17β-carboxylic acid (3.484 grams; 10 millimoles) was dissolved into methylalcohol. A 10 milliliter solution of 1 normal KOH in methanol was added dropwise to the cold mixture. The solution was evaporated under vacuo and the residue was dried thoroughly and taken up into 20 milliliters dimethylsulfoxide and 2.5 milliliters methyliodide (48 millimoles). After stirring overnight at room temperature, the mixture was diluted with 150 milliliters ethylacetate and washed successively with 50 milliliters NaHCO3 (3% weight/volume), 50 milliliters Na2S2O3 (5% weight/volume) and three additional times with 50 milliliters water. The mixture was dried over MgSO4 and evaporated. The product crystallized from the ethylacetate, and 3 crops gave 3.31 grams (92%) of white crystals melting at 206° C. to 207° C. (little at 207° C. to 208° C.). $^1$H nmr (CDCl3) 0.98 (S,3,18C$\underline{H}$3); 1.45 : (S,3,19C$\underline{H}$3); 3.75 (S,3,COOC$\underline{H}$3); 5.67 (S,1,$\overline{C}$=CH). The product, methyl 11β,17α-dihydroxyandrost-4-en-3-one-17β-carboxylate, can be represented by the structural formula:

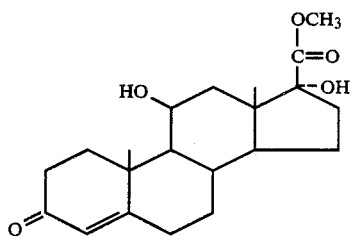

EXAMPLE 6

The methyl 11β-17α-dihydroxyandrost-4-en-3-one-17β-carboxylate (10.332 grams; 22.5 millimoles) was taken into 178 milliliters of ethylene glycol, then 85 milligrams of p-toluenesulfonic acid (anhydrous, crystallized from benzene) was added. The solvent was slowly distilled off at 0.3–1 mm Hg for two hours. The distillation head was 60° C. to 70° C. and the mixture turned red after about 30 minutes when the compound started to precipitate. The suspension was neutralized with NaHCO₃ (the mixture turned colorless), then the suspension was poured into 200 milliliters of cold water and stirred for at least 30 minutes. The white precipitate was isolated by filtration, washed with water and dried in a freeze dryer. Thin layer chromatography showed a small amount of starting material and a few percent of a product that was identified as the Δ9.11 3,3' cyclic ketal. Triturating the product with a few milliliters of ether yielded white crystals of melting point 204° C. to 205° C. that had satisfactory elemental analysis. Required: C67.96; H8.43; Found: C67.71; H8.47. ¹H nmr (CDCl₃): 0.93 (S,3,18CH₃); 1.27 (S,3,19CH₃) 3.70 S,3,COOCH₃); 3.90 (S,4,OCH₂CH₂O); 5.12 (S,1,C=CH). The product, methyl 11β,17α-dihydroxyandrost-5-en-3-(1',3'-dioxacyclopent-2'-yl)-17β-carboxylate, can be represented by the structural formula:

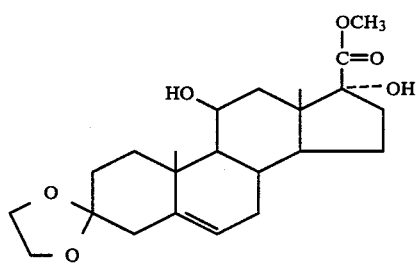

EXAMPLE 7

Powdered KOH (1.2 grams) was stirred 5 minutes into 15 milliliters dimethylsulfoxide, then 2.15 grams methyl 11β,17α-dihydroxyandrost-5-en-3-(1',3'-dioxacyclopent-2'-yl)-17β-carboxylate (5.3 millimoles) was added. This was immediately followed by the addition of 1.7 milliliters iodoethane (21.2 millimoles) and the mixture was stirred at 25° C. for 23 hours. The reaction mixture was then diluted with 158 milliliters ethylacetate and washed successively with 50 milliliters Na₂S₂O₃ (5% weight/volume), and three times with 50 milliliters water. The mixture was then dried over MgSO₄ and evaporated to give 1.92 grams of a crude product (83% theoretical). Some product had been extracted in the aqueous phase and was identified as cortienic acid-3,3'cyclic ketal. Purification from 45 grams of silica gel, eluting with benzene/EtOAc 80:20 yielded 1.1 gram of a white compound. IR (KBr): 3500, 1725, 1215, 1110, 1085 cm⁻¹. H nmr 0.90 (S,3,18CH₃); 1.10 (T,3,J=7 Hz, OCH₂CH₃); 1.28 (S,3,19CH₃); 3.32 (M,2,OCH₂CH₃) 3.70 (S,3,COOCH₃); 3.95 (S,4,OCH₂CH₂O); 5.15 (S,1,C=CH). The product, methyl 11β-hydroxy-17α-ethoxyandrost-5-en-3-(1',3'-dioxacyclopent-2'-yl)-17β-carboxylate, can be represented by the structural formula:

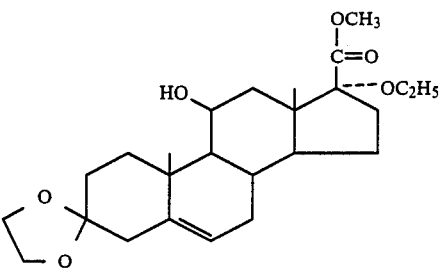

Substitution of an equivalent quantity of iodopropane for iodoethane employed above and substantial repetition of the foregoing procedure afforded methyl 11β-hydroxy-17α-propoxyandrost-4-en-3-(1',3'-dioxacyclopent-2'-yl)-17β-carboxylate, having an identical H nmr spectrum to that presented above without the triplet of 1.10 ppm.

Substitution of bromobutane for iodoethane at a ratio of 4 parts bromobutane per part methyl 11β,17α-dihydroxyandrost-5-en-3-(1',3'-dioxacyclopent-2'-yl)-17β-carboxylate and substantial repetition of the foregoing procedure while allowing the reaction to proceed for three days afforded methyl 11β-hydroxy-17α-butoxyandrost-5-en-3-(1',3'-dioxacyclopent-2'-yl)-17β-carboxylate. The crude product was a mixture of the methyl of the methyl and butyl ester.

EXAMPLE 8

The methyl 11β-hydroxy-17α-ethoxyandrost-4-en-3-(1',3'-dioxacyclopent-2'-yl)-17β-carboxylate (1.1 grams, 2.5 millimoles), the first product described in Example 7, was stirred for 17 hours under nitrogen at 60° C. in 5 milliliters dimethyl sulfoxide containing 0.5 grams of powdered KOH. The reaction was then taken up into 150 milliliters of water, acidified slowly with dilute HCl to pH 1.2, stirred for fifteen minutes and extracted four times with 80 milliliters EtOAc. The mixture was dried over MgSO₄ and evaporated. The crude product was dissolved in NaHCO₃ (3% weight/volume), washed with EtOAc and acidified. Drying gave 669 milligrams (64%) of acid (11). IR (KBr): 3500, 1715, 1670, 1085 cm⁻¹. H nmr (DMSOd6): 0.92 (S,3,18CH₃); 1.05 (T,3,J=7 Hz, OCH₂CH₃); 1.37 (S,3,19CH₃); 3.28 (M,2,OCH₂CH₃); 5.55 (S,1,C=CH). The product, 11β-hydroxy-17α-ethoxyandrost-4-en-3-one-17β-carboxylic acid, can be represented by the structural formula:

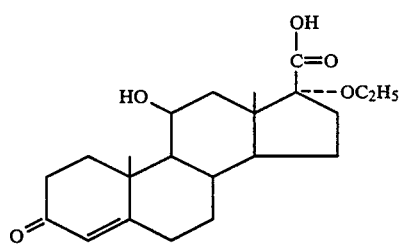

Likewise, the second and third products described in Example 7 were subjected to substantially the same procedure described above. The products obtained were 11β-hydroxy-17α-propoxyandrost-4-en-3-one-17β-carboxylic acid and 11β-hydroxy-17α-butoxyandrost-4-en-3-one-17β-carboxylic acid, respectively.

EXAMPLE 9

The potassium salt of the first product of Example 8, 11β-hydroxy-17α-ethoxyandrost-4-en-3-one-17β-carboxylic acid (1.58 millimole) was prepared in substantially the same manner as the potassium salt of Example 4. That is, the first product of Example 8 was stirred at room temperature for eight hours in 10 milliliters dimethylsulfoxide containing 1.25 milliliters chloroiodomethane. The work-up described in Example 4 was followed and 0.594 gram of a crude product was obtained that was chromatographed on 15 grams silica gel, eluting with Hexane/EtOAc 80:20 then 70:30. Crystallization from $CH_2Cl_2$/Pentane gave white crystals melting at 203° C. to 205° C. IR (KBr): 3400, 1750, 1650, 1205, 1110, 1060 cm$^{-1}$. H nmr (CDCl$_3$): 0.95 (S,3,18CH$_3$); 1.13 (T,3,J-7 Hz;OCH$_2$CH$_3$); 1.43 (S,3,19C$\overline{H}_3$); 3.38 (M,2,OC$\overline{H}_2$CH$_3$); 5.65 (S,$\overline{1}$,C=C$\overline{H}$); 5.77 (S,$\overline{2}$,COOC$\overline{H}_2$Cl). Elemental analysis: Required: C65:08; H7.83; $\overline{C}$18.34 Found: C64.86, H7.84; C18.32. The product, chloromethyl 11β-hydroxy-17α-ethoxyandrost-4-en-3-one-17β-carboxylate, can be represented by the structural formula:

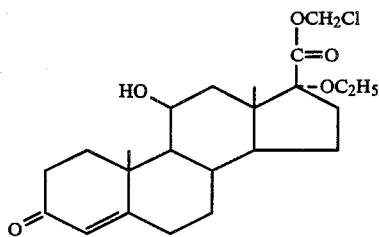

Likewise, the second and third products described in Example 8 were subjected to substantially the same procedure described above.

The product, chloromethyl 11β-hydroxy-17α-propoxyandrost-4-en-3-one-17β-carboxylate, had a melting point of 194° C. to 195° C. IR(KBr): 3400; 1750, 1650, 1205, 1110, 1060, 1030 cm$^{-1}$ H nmr (CDCl$_3$): 0.88 (T,3,J=7 Hz, OCH$_2$CH$_2$CH$_3$); 0.98 (S,3,18CH$_3$); 1.42 (S,3,19CH$_3$); 3.18 (M,$\overline{2}$,OCH$_2$CH$_2$CH$_3$); 5.65 (S,1,C=C$\overline{H}$); 5.77 (S,2,COOC$\overline{H}_2\overline{Cl}$). Elemental analysis: Required: C65.66; H8.04; $\overline{C}$18.08; Found: C65.78; H8.09; C18.14.

The product, chloromethyl 11β-hydroxy-17α-butoxyandrost-4-en-3-one-17β-carboxylate, had a melting point of 150° C. to 151° C. IR(KBr): 3400, 1750, 1645, 1200, 1110(ether), 1070(11βOH) H nmr (CDCl$_3$): 0.98 (S,3,18CH$_3$); 1.45 (S,3,19CH$_3$); 3.28 (M, 2,OC$\overline{H}_2\overline{C}H_2$CH$_3$); 5.65 (S,$\overline{1}$,C=C$\overline{H}$); 5.77 (9,2,$\overline{C}$OOC$\overline{H}_2$Cl).

EXAMPLE 10

Methoxy 11β,17α-dihydroxy-1,4-diene-3-one-17β-carboxylate (prednisolone) (30 grams; 0.08 moles) was placed in a solution of tetrahydrofuran and methanol. A warm water solution of 53 grams NaIO$_4$ was added dropwise. The reaction mixture was stirred for two hours at room temperature, then while the stirring was continued, ice water was added to obtain crystalline materials. The crude crystals were washed with water then stirred and suspended in 800 milliliters of water for 30 minutes. The crystals were filtered, washed with water and dried. The colorless crystal product weighed 27 grams (77 millimoles) which represents a 97% yield and had a melting point of 236° C. to 238° C. The product, 11β,17α-dihydroxy-1,4-diene-3-one-17β-carboxylic acid, can be represented by the formula:

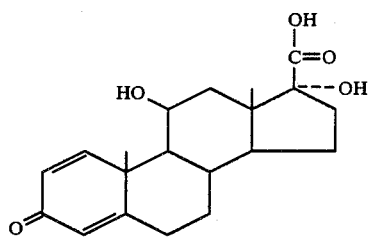

EXAMPLE 11

To an ice cooled mixture of 11β,17α-dihydroxy-1,4-diene-3-one-17β-carboxylic acid (5.2 grams; 15 millimoles) as prepared in Example 10 and KOH (6.7 grams; 12 moles) in 30 milliliters of dimethylsulfoxide was added 3.7 milliliters methyliodide (60 millimoles) under nitrogen. The mixture was stirred for 5 hours at room temperature. The reaction mixture was diluted with ethyl acetate. The organic phase was separated and washed successively with water, Na$_2$S$_2$O$_3$ solution, NaHCO$_3$ solution and finally with water. The mixture was dried over MgSO$_4$ and the solvent was evaporated. The resulting crystalline material was recrystallized from CH$_2$Cl$_2$ hexane to afford colorless prisms. The product weighed 2.7 grams (7.2 millimoles) which represents an 83% yield and had a melting point of 241° C. to 246° C. C$_{22}$N$_{30}$O$_5$ 374.47: Theoretical: H 8.07; C 70.56; Found: H 8.13; C 70.54. The product, methyl 11β-hydroxy-17α-methoxy-3-oxo-androsta-1,4-diene-17β-carboxylate, can be represented by the formula:

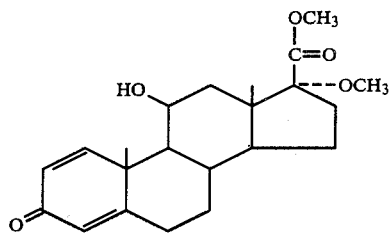

In a similar manner, substitution of an equivalent quantity of propyl iodide (5.8 milliliters; 60 millimoles) for the methyl iodide employed in the first part of this example and substantial repetition of the procedure there detailed affords 1.9 gram propyl 11β-hydroxy-17α-propoxy-androsta-1,4-diene-3-one-17β-carboxylate (4.4 moles; 29% yield). The final product, after crystallization from CH$_2$Cl$_2$ hexane, melts at 189° C. to 190° C. C$_{26}$H$_{38}$O$_5$ 430.58: Theoretical: H 8.99; C 72.53; Found: H 9.04; C 72.26.

EXAMPLE 12

A mixture of 5.4 grams KOH (9 millimoles) and 4.5 grams methyl 11β-hydroxy-17α-methoxy-androsta-1,4-diene-3-one-17β-carboxylate in 20 milliliters dimethylsulfoxide was stirred under nitrogen for five hours at 50° C. Water was added to the reaction mixture and the mixture was then acidified with 10% HCl. The reaction mixture was stirred for 30 minutes. The ethylacetate extract was washed with water and the solvent was evaporated. The residual solid was neutralized with sodium bicarbonate solution and the mixture was washed with dichloromethane. The aqueous phase was acidified with 10% HCl and the deposited crystalline material was filtered under suction. The dried crude crystals were washed with water and dried. The crude product was subjected to silica gel chromatograph (MeOH/CH$_2$Cl$_2$)=1/200-1/50). The product so obtained was recrystallized from methanol. The colorless prism product was 2.3 grams (6.4 millimoles) which represents yield of 53% and had a melting point of about 256° C. to 257° C. C$_{21}$H$_{28}$O$_5$: 360.44: Theoretical: H 7.83; C 69.98; Found: H 8.02; C 70.01. The product, 11β-hydroxy-17α-methoxy-androsta-1,4-diene-3-one-17β-carboxylic acid, can be represented by the formula:

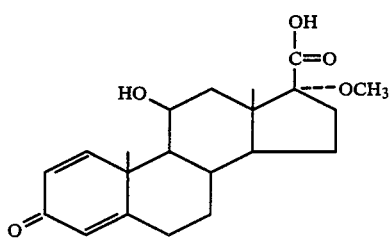

In a similar manner, the second product of Example 11, propyl 11β-hydroxy-17α-propoxy-androsta-1,4-diene-3-one-17β-carboxylate (1.6 gram; 3.7 millimoles) and 1.8 gram KOH (32 millimoles) in 20 milliliters dimethylsulfoxide was heated at 50° C. under stirring in nitrogen for 20 hours. The crude acid was worked up and chromatographically purified (MeOH/CH$_2$Cl$_2$=1/500-1/30). Recrystallization from ether afforded 0.62 grams 11β-hydroxy-17α-propoxy-androsta-1 4-diene-3-one-17β-carboxylic acid representing a 43% yield and had a melting point of 223° C. to 25° C. C$_{23}$H$_2$O$_5$: 388.50: Theoretical: H 8.30; C 71.11; Found: H 8.47; C 71.05.

EXAMPLE 13

To 5 milliliters of 1 normal KOH/MeOH solution which was cooled with ice, was added 1.8 gram 11β-hydroxy-17α-methoxyandrosta-1,4-diene-3-one-17β-carboxylic acid. The mixture was worked up to dryness under vacuum. The dried mixture was dissolved in 5 milliliters dimethylsulfoxide then 3.6 grams chloroiodomethane (20 millimoles) was added. The reaction mixture was stirred at room temperature for six hours. The ethylacetate extract was washed with water, sodium thiosulfate solution, sodium bicarbonate solution and finally with water. The solution was dried over MgSO$_4$ and the solvent was evaporated. After silica column chromatography (MeOH/CH$_2$Cl$_2$=2-50-1/100), the product was recrystallized from ethylacetate. The colorless prism product was 0.46 gram (1.1 millimoles) representing a yield of 22% and had a melting point of 217° C. to 218° C. C$_{22}$H$_{29}$ClO$_5$: 408.92: Theoretical: H 7.15; C 64.62; Found: H 7.24; C 64.48. The product, chloromethyl 11β-hydroxy-17α-methoxy-androsta-1,4-diene-3-one-17β-carboxylate, can be represented by the formula:

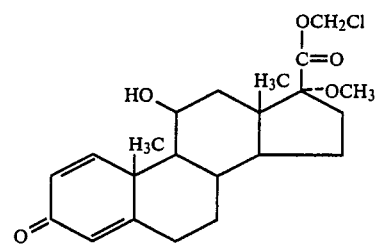

In a similar manner, the second product of Example 12, 11β-hydroxy-17α-propoxy-androsta-1,4-diene-3-one-17β-carboxylic acid (0.55 gram; 1.4 millimole) was heated at the same manner to the first part of this example. Substantial repetition of the procedure there detailed afforded 34 milligrams chloromethyl 11β-hydroxy-17α-propoxy-androsta-1,4-diene-3-one-17β-carboxylate (0.08 millimoles) which represents a yield of 6% and a melting point of 184° C. to 187° C. C$_{24}$H$_{33}$ClO$_5$: 436.97: Theoretical: H 7.61; C 65.97; Found: H 7.74; C 65.65.

EXAMPLE 14

To a suspension of 11β,17α-dihydroxyandrost-4-en-3-one 17β-carboxylic acid (cortienic acid; 3.0 grams) in acetonitrile (30 milliliters) was added triethylamine (1.2 milliliters) followed by chloromethylmethylsulfide (ClCH$_2$SCH$_3$). The resulting solution was refluxed overnight. After cooling at room temperature, the solvent was evaporated and the residue was triturated with tetrahydrofuran (30 milliliters). The precipitate was filtered off and washed with additional tetrahydrofuran. The filtrates were combined and evaporated under reduced pressure to obtain 3.0 grams of product having the following: H nmr (CDCl$_3$): 1.06 (s, 3, 18CH$_3$); 1.47 (s, 3, 19CH$_3$); 2.30 (s, 3, SCH$_3$); 4.52 (m, 1, 11C$\overline{\text{H}}$); 5.27 (s, 2, OC$\overline{\text{H}}_2$SCH$_3$); 5.73 (s, 1, C=CH). The product, methylthiomethyl 11β,17α-dihydroxyandrost-4-en-3-one-17β-carboxylate, can be represented by the structural formula:

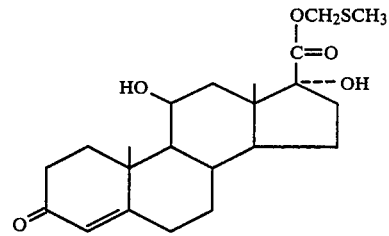

EXAMPLE 15

The methylthiomethyl 11β,17α-dihydroxyandrost-4-en-3-one-17β-carboxylate (0.817 gram) was stirred for 10 minutes in pyridine (10 ml) at −15° C. and trifluoroacetic anhydride (1.1 equivalent) was added dropwise. After stirring for 15 minutes at −15° C., the cold bath was removed and the solution was allowed to slowly warm up to room temperature and poured into cold brine (100 milliliters). The resulting precipitate was stirred for 30 minutes and filtered off, washed with water and dried. The dried product was purified from 30 grams of silica gel and eluted with EtOAc/Hexane 20 to 60% and gave 0.75 gram of final product having the following elemental analysis: H nmr (CDCl$_3$): 0.92

(s, 3, 18CH$_3$); 1.29 (s, 3, 19CH$_3$); 2.24 (s, 3, SCH$_3$); 5.24 (ABq,Δν=0.13 ppm; J$_{AB}$=12 Hz, CH$_2$SCH$_3$O); 5.71 (m, 1, 11CH); 5.76 (s, 1, C=CH). IR (CDCl$_3$): 3400, 1780, 1730, 1670 cm$^{-1}$. The product, methylthiomethyl 17α-hydroxy-11β-trifluoroacetoxyandrost-4-en-3-one-17β-carboxylate, can be represented by the structural formula:

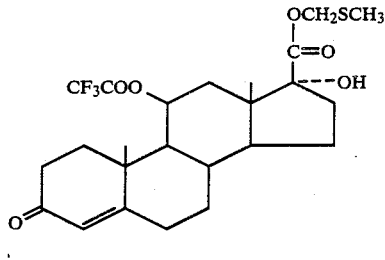

EXAMPLE 16

The methylthiomethyl 17α-hydroxy-11β-trifluoroacetoxyandrost-4-en-3-one-17β-carboxylate (0.75 gram) was dissolved in 20 milliliters of a mixture containing equal parts (volume/volume) of dimethylsulfoxide and acetic anhydride. The solution was stirred for two days at room temperature under an atmosphere of nitrogen, concentrated under vacuo (1-2 mm Hg) and poured into a saturated NaHCO$_3$ solution (200 milliliters). After stirring an additional hour, the precipitate was filtered off, washed with water and dried to obtain 0.744 gram of product having the following elemental analysis: H nmr (CDCl$_3$): 0.90 (s, 3, 18CH$_3$); 1.30 (s, 3, 19CH$_3$); 2.18 (s, 3, SCH$_3$); 2.24 (s, 3 SCH$_3$); 4.44 (ABq, Δν=0.07 ppm, J$_{AB}$=12 Hz, OCH$_2$SCH$_3$); 5.22 (ABq, Δν=0.29 ppm, J$_{AB}$=12 Hz, COOCH$_2$SCH$_3$). IR (KBr): 1780, 1730, 1670cm$^{-1}$. The product, methylthiomethyl 17α-methylthiomethyloxy-11β-trifluoroacetoxyandrost-4-en-3-one-17β-carboxylate, can be represented by the structural formula:

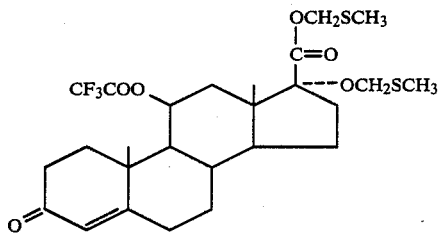

EXAMPLE 17

The methylthiomethyl 17α-methylthiomethyloxy-11β-trifluoroacetoxyandrost-4-en-3-one-17β-carboxylate (0.677 grams) was refluxed for four hours in wet methanol (10 milliliters) containing sodium bicarbonate (150 milligrams). The solution was then poured into cold stirring water (100 milliliters) and stirred another 30 minutes. The precipitate was filtered off, washed with water and dried.

The pure final product, from silica gel chromatography (17 g), eluting with EtOAc/Hexane 30:70 and crystallization from CH$_2$Cl$_2$/Pentane, had a melting point of 195° C. to 196° C. H nmr (CDCl$_3$): 1.01 (s, 3, 18CH$_3$); 1.46 (s, 3, 19CH$_3$); 2.19 (s, 3, SCH$_3$); 2.41 (s, 3, SCH$_3$); 4.44 (m, 3, OCH$_2$s and 11CH); 5.21 (ABq, Δν=0.06 ppm, J$_{AB}$=12 Hz, COOCH$_2$S); 5.71 (s, 1, C=CH). IR (KBr): 3400, 1730, 1655cm$^{-1}$. The product, methylthiomethyl 11β-hydroxy-17α-methylthiomethyloxyandrost-4-en-3-one-17β-carboxylate, can be represented by the structural formula:

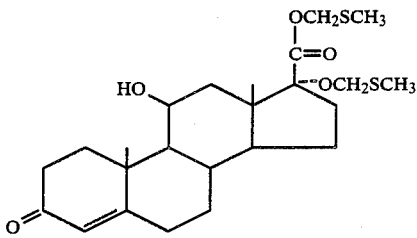

EXAMPLE 18

11β,17α-dihydroxy androst-4-en-3-one-17β-carboxylic acid (cortienic acid; 3.48 grams) was suspended in methanol (10 milliliters) and a 1 normal solution of KOH in methanol (10 milliliters) was added dropwise. After concentration under vacuo and drying, the potassium salt was taken up into dimethylsulfoxide (10 milliliters) and treated with chloroiodomethane (1.5 milliliters). The reaction mixture was stirred at room temperature for five hours, partitioned between CH$_2$Cl$_2$ (100 milliliters) and water (100 milliliters). The organic layer was washed successively with 50 milliliters Na$_2$S$_2$O$_3$ (5% weight/volume), 50 milliliters of 5% NaHCO$_3$ and twice with 50 milliliters water. The product was dried over MgSO$_4$, filtered and evaporated, giving a mixture containing the desired product plus a compound which was a diner of the starting material. The pure compound had a melting point of 100° C. to 192° C. The product, chloromethyl 11β,17α-dihydroxyandrost-4-en-3-one-17β-carboxylate, can be represented by the structural formula:

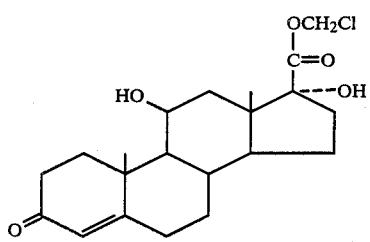

EXAMPLE 19

Chloromethyl 11β,17α-dihydroxyandrost-4-en-3-one-17β-carboxylate (3.48 grams) was reacted following the same procedure as in Example 15. Analysis: H nmr (CDCl$_3$): 0.91 (s, 3, 18CH$_3$); 1.30 (s, 3, 19CH$_3$); 5.73 (m, 4, C=CH plus 11CH plus COOCHCl) The product, chloromethyl 17α-hydroxy-11β-trifluoroacetoxyandrost-4-en-3-one-17β-carboxylate, can be represented by the structural formula:

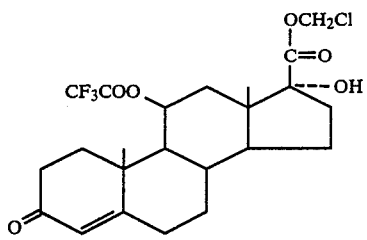

EXAMPLE 20

Chloromethyl 17α-hydroxy-11β-trifluoroacetoxyandrost-4-en-3-one-17β-carboxylate (3.48 grams) was reacted following the same procedure in Example 16. The final product had the following elemental analysis: H nmr (CDCl$_3$): 0.90 (s, 3, 18CH$_3$); 1.33 (s, 3, 19CH$_3$); 2.24 (s, 3, SCH$_3$); 4.43 (ABq, Δν̄=0.11 ppm, J$_{AB}$=11 Hz, OCH$_2$S); 5.74 (m, 4, C=CH plus 11CH plus COOCH$_2$Cl). The product, chloromethyl 17α-methylthiomethyloxy-11β-trifluoroacetoxyandrost-4-en-3-one-17β-carboxylate, can be represented by the structural formula:

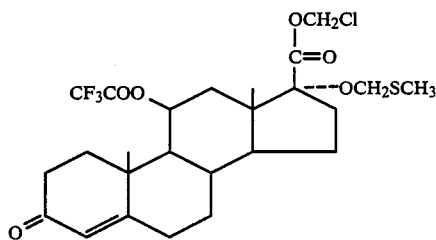

EXAMPLE 21

The chloromethyl 17α-methylthiomethyloxy-11β-trifluoroacetoxyandrost-4-en-3-one-17β-carboxylate, was reacted following the same procedure as Example 17. The final product had the following elemental analysis: H nmr (CDCl$_3$): 1.00 (s, 3, 18CH$_3$); 1.30 (s, 3, 19CH$_3$); 2.18 (s, 3 SCH$_3$); 4.41 (ABq, Δν̄=0.06 ppm; J$_{AB}$=6 Hz; OCH$_2$S); 4.44 (m, 1, 11CH); 5.67 (s, 1, C=CH); 5.77 (ABq, Δν=0.06ppm, J$_{AB}$=6 Hz; COOCH$_2$Cl). The product, chloromethyl 11β-hydroxy-17α-methylthiomethyloxyandrost-4-en-3-one-17β-carboxylate, can be represented by the structural formula:

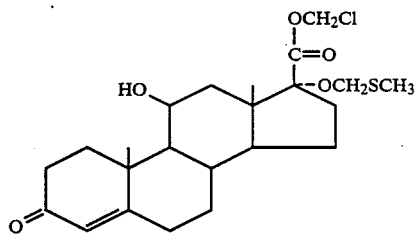

EXAMPLE 22

Powdered potassium hydroxide (2.14 grams) was stirred for five minutes into dimiethylsulfoxide (10 milliliters). 11β-17α-Dihydroxy androst-4-en-3-one-17β-carboxylic acid (cortienic acid; 1.7 grams; 4.88 millimoles) was immediately added followed by methyliodide (1.22 milliliters; 19.5 millimoles). After stirring for one hour and 15 minutes at 25° C., the mixture was diluted with ethylacetate (100 milliliters) and washed successively with 10 milliliters water, 10 milliliters Na$_2$S$_2$O$_3$ (5% weight/volume), 10 milliliters NaHCO$_3$ (5% weight/volume) and three more times with 10 milliliters water. The organic solution was then dried over MgSO$_4$ and evaporated under partial pressure. The white, crystalline, crude product weighed 1.73 grams (94% theoretical) and had a melting point of 195° C. to 201° C. Crystallization from CH$_2$Cl$_2$/Pentane raised the melting point to 215° C. to 217° C., then 217° C. to 218.5° C. Elemental analysis: required C70.18; H8.57; found C70.16; H8.62. IR (KBr): 3500, 1725, 1655, 1210 cm$^{-1}$, H nmr (CDCl$_3$): 0.93 (s, 3, 18CH$_3$); 1.43 (s, 3, 19CH$_3$); 3.10 (s, 3, 17OCH$_3$); 3.72 (s, 3, COOCH$_3$); 5.65 (s, 1, C=CH). The product, methyl 11β-hydroxy-17α-methoxyandrost-4-en-3-one-17β-carboxylate, can be represented by the structural formula:

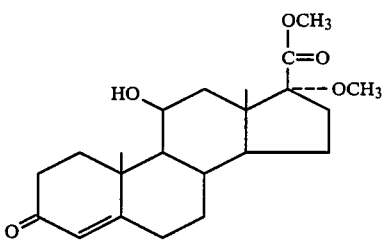

EXAMPLE 23

The methyl 11β-hydroxy-17α-methoxyandrost-4-en-3-one-17β-carboxylate, (3.76 grams; 10 millimoles), was stirred overnight (16 hours) at 50° C., under nitrogen, in a mixture compound of powdered potassium hydroxide (4.50 grams) and dimethylsulfoxide (15 milliliters). The reaction mixture is then diluted into water (200 milliliters), acidified with Hcl, stirred 30 minutes and extracted with several portions of ethyl acetate. The organic layer was then washed with water (30 milliliters), evaporated and taken up into 150 milliliters of NaHCO$_3$ solution (5% weight/volume). This aqueous solution was washed with 30 ml of methylene chloride, acidified with diluted HCl, filtered, and the residue is dried in vacuo at 40° C. overnight. The yellow, pseudocrystalline, crude product weighed 3.05 g (84% theor.). Elemental analysis: $^1$H nmr (DMSOd$_6$): 0.92 (s, 3, 18CH$_3$); 1.38 (s, 3, 19CH$_3$); 3.04 (s, 3, OCH$_3$); 5.50 (s, 1, C=CH); 8.28 (s, <1, COOH). Purification from Silica gel (CCl$_4$), eluting with EtOAc/Hexane 50:50 and crystallization from acetone gave a compound melting at 214° C. to 216° C., with satisfactory elemental analysis. The product, 11β-hydroxy-17α-methoxyandrost-4-en-3-one-17β-carboxylic acid, can be represented by the structural formula:

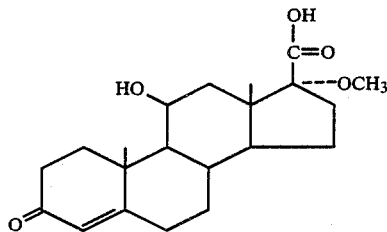

EXAMPLE 24

The 11β-hydroxy-17α-methoxyandrost-4-en-3-one-17β-carboxylic acid, (1 millimole) was suspended in methanol (5 milliliters) and a 1 normal solution of KOH in methanol (1 milliliter) was added dropwise at 0° C. (ice bath). The solution was evaporated under vacuo, dried thoroughly, and the resulting potassium salt was mixed with dimethylsulfoxide (10 milliliters) and chloroiodomethane (4 millimoles). After stirring for 7 hours at room temperature (24° C.), the mixture (containing a precipitate of potassium iodide) was diluted with ethylacetate (100 milliliters) and washed successively with 10 milliliters water, 10 milliliters $Na_2S_2O_3$ (5% weight/volume), 10 milliliters $NaHCO_3$ and 3 times with water (10 milliliters) and dried over $MgSO_4$ and evaporated under partial pressure. Purification by column chromatography from 12 grams of Silica gel (100–200 mesh type 60A) eluting with $EtOAc/CHCl_3$ 20:80 and crystallization from ethylacetate/ether gave a product that melts at 195° C. to 196° C. $^1H$ nmr ($CDCl_3$): 0.95 (s, 3, $18CH_3$); 1.43 (s, 3, $19CH_3$); 3.12 (s, 3, $OCH_3$); 5.60 (s, 1, C=CH); 5.75 (s, 2, $COOCH_2Cl$). IR (KBr): 3400, 1755, 1655, 1205, 2110 (ether) $cm^{-1}$. Elemental analysis: Required: C64.30; H760; C18.63; found: C64.16; H7.63; C18.63. The product, chloromethyl 11β-hydroxy-17α-methoxyandrost-4-en-3-one-17β-carboxylate, can be represented by the represented by the formula:

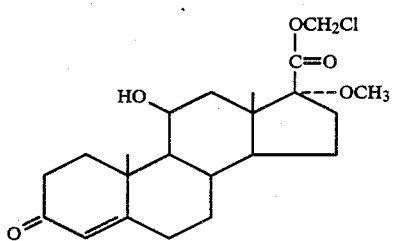

EXAMPLE 25

11β,17α-Dihydroxyandrost-4-en-3-one 17β-carboxylic acid (cortienic acid; 3.434 grams; 10 millimoles) was dissolved in methylalcohol, then a 1 normal solution of KOH in MeOH (10 milliliters) was added dropwise in the cold. The solution was evaporated under vacuo and the residue was dried thoroughly and taken up into dimethylsulfoxide (20 milliliters) and methyliodide (2.5 milliliters; 40 millimoles). After stirring overnight at room temperature, the mixture was diluted with ethylacetate (15 milliliters) and washed successively with 50 milliliters $NaHCO_3$ (3% weight/volume), 50 milliliters $Na_2S_2O_3$ (5% weight/volume) and three times with 50 milliliters water, dried over $MgSO_4$ and evaporated. The product crystallized from ethylacetate, and 3 crops gave 3.31 g (92%) of white crystals melting at 206° C. to 207° C. (litt. 207° C. to 208° C.). $^1H$ nmr ($CDCl_3$): 0.98 (s, 3, $18CH_3$); 1.45 (s, 3, $19CH_3$); 3.75 (s, 3, $COOCH_3$); 5.67 (s, 1, C=CH). The product, methyl 11β,17α-dihydroxyandrost-4-en-3-one-17-carboxylate, can be represented by the structural formula:

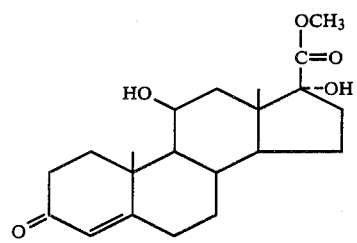

EXAMPLE 26

The methyl 11β,17α-dihydroxyandrost-4-en-3-one-17β-carboxylate, (10.32 grams; 22.5 millimoles), was taken up into ethylene glycol (170 milliliters) and p-toluenesulfonic acid (anhydrous, crystallized from benzene; 85 milligrams) was added. The solvent was slowly distilled off at 0.3–1 mm Hg for 2 hours. The distillation lead was 60° C. to 70° C. and the mixture turned red after about 30 minutes. The suspension was neutralized with $NaHCO_3$ (the mixture turned colorless), poured into cold water (200 milliliters) and stirred for at least 30 minutes. The white precipitate was isolated by filtration, washed with water and dried in the freeze dryer. Thin layer chromatography showed a small amount of starting material and a few percent of a product identified as the $\Delta^{9,11}$ 3,3' cyclic ketal. Triturating the product with a few milliliters of ether yielded white crystals having a melting point of 204° C. to 205° C. with satisfactory elemental analysis. Theoretical: C67.96; H8.43; Found: C67.71; H8.47. $^1H$ nmr ($CDCl_3$): 0.93 (s, 3, $18CH_3$); 1.27 (s, 3, $19CH_3$); 3.70 (s, 3, $COOCH_3$); 3.90 (s, 4, $OCH_2CH_2O$); 5.12 (s, 3, $19CH_3$); 3.70 (s, 3, $COOCH_3$); 3.90 (s, 4, $OCH_2CH_2O$); 5.12 (s, 1, C=CH). The product, methyl 3-(1',3'-dioxacyclopent-2'-yl)-11β,17α-dihydroxyandrost-5-en-3-one-17β-carboxylate, can be represented by the structural formula:

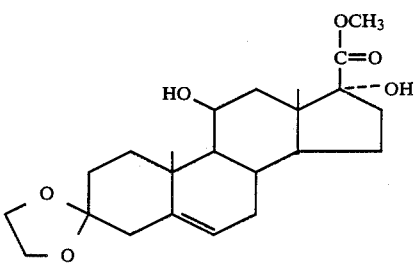

EXAMPLE 27

Powdered KOH (1.2 grams) was stirred for five minutes into dimethylsulfoxide (15 milliliters), then the methyl 3-(1',3'-dioxacyclopent-2'-yl)-11β,17α-dihydroxyandrost-5-en-3-one-17β-carboxylate (2.15 grams; 5.3 millimoles) was added, immediately followed by iodoethane (1.7 milliliters, 21.2 millimoles) and the mixture was stirred at 25° C. for 23 hours. The reaction was then diluted with ethylacetate (150 milliliters) and washed successively with 50 milliliters $Na_2S_2O_3$ (5% weight/volume) and three times with 50 milliliters water, dried over $MgSO_4$ and evaporated to give 1.92 grams of crude product (83% theoretical). Some product was extracted with the aqueous phase and was identified as cortienic acid-3,3' cyclic ketal. Purification from 45 grams of silica gel and eluting with benzene/EtOAc 80:20 yielded 1.1 g of a white compound. IR (KBr): 3500, 1725, 1215, 1110, 1085 cm$^{-1}$. H nmr 0.90 (s, 3, 18C$\underline{H}_3$); 1.10 (t,3, J=7 Hz, OCH$_2$C$\underline{H}_3$); 1.28 (s, 3, 19C$\underline{H}_3$); 3.32 (m, 2, OC$\underline{H}_2$CH$_3$) 3.70 (s, 3, COOC$\underline{H}_3$); 3.95 (s, 4, OC$\underline{H}_2$CH$_2$O); 5.15 (s, 1, C=C$\underline{H}$). The product, methyl 3-(1',3'-dioxacyclopent-2'-yl)-17α-ethoxy-11β-hydroxyandrost-5-en-3-one-17β-carboxylate, can be represented by the structural formula:

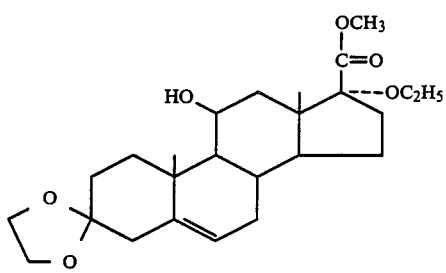

EXAMPLE 28

The methyl 3-(1',3'-dioxacyclopent-2'-yl)-11β,17α-dihydroxyandrost-5-en-3-one-17β-carboxylate and iodopropane were reacted following the same procedure in Example 27. The H nmr spectrum was identical (without the triplet at 1.10 ppm). The product, methyl 3-(1',3'-dioxacyclopent-2'-yl)-11β-hydroxy-17α-propoxyandrost-5-en-3-one-17β-carboxylate, can be represented by the following structural formula:

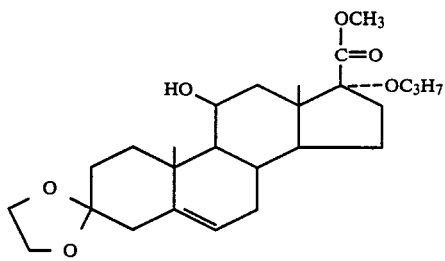

EXAMPLE 29

The methyl 3-(1',3'-dioxacyclopent-2'-yl)-11β,17α-dihydroxyandrost-5-en-3-one-17β-carboxylate and bromobutane were reacted following the same procedure in Example 25 except that a ratio of 4:1 of bromobutane to the 17α-hydroxy compound was used and the reaction was allowed to proceed for three days. The crude product was a mixture of the methyl and butyl ester. The butyl ester, methyl 3-(1',3'-dioxacyclopent-2'-yl)-17α-butoxy-11β-hydroxyandrost-5-en-3-one-17β-carboxylate, can be represented by the structural formula:

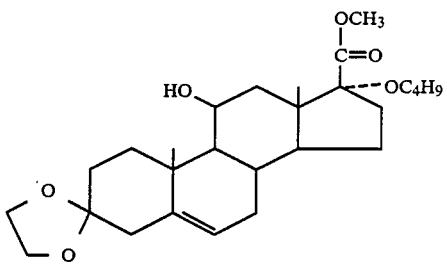

EXAMPLE 30

The chloromethyl 11β-hydroxy-17α-methylthiomethyloxy-androst-4-en-3-one-17β-carboxylate (1.1 grams; 2.5 millimoles) was stirred for 17 hours under nitrogen at 60° C. in dimethylsulfoxide (5 milliliters) containing powdered KOH (0.5 gram). The reaction was then taken up into water (150 milliliters), acidified slowly with dilute HCl to pH 1-2, stirred for 15 minutes and extracted four times with EtOAc (80 milliliters), dried over MgSO$_4$ and evaporated. The crude product was dissolved into NaHCO$_3$ (13% weight/volume), washed with EtOAc and acidified. Drying gave 669 mg (64%) of product. IR (KBR): 3500, 1715, 1670, 1085 cm$^{-1}$. H nmr (DMSOd$_6$): 0.92 (s, 3, 18CH$_3$); 1.05 (t, 3, J=7H$_z$,OCH$_2$C$\underline{H}_3$); 1.37 (s, 3, 19C$\underline{H}_3$); 3.28 (m, 2, OC$\underline{H}_2$CH$_3$); 5.55 (s, 1, C=C$\underline{H}$). Purification from CCl$_4$ silica gel and crystallization from acetone gave a compound melting at 236° C. to 240° C. with satisfactory elemental analysis. The product, 17α-ethoxy-11β-hydroxyandrost-4-en-3-one-17β-carboxylic acid, can be represented by the structural formula:

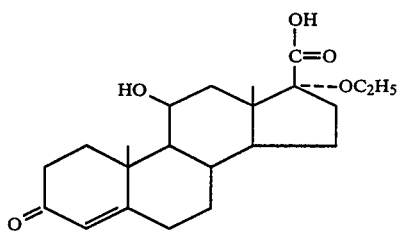

EXAMPLE 31

11β-Hydroxy-17α-propoxyandrost-4-en-3-one-17β-carboxylic acid and 17α-butoxy-11β-hydroxyandrost-4-en-3-one-17β-carboxylic acid were prepared following a similar procedure to Example 30 and gave satisfactory elemental analysis.

EXAMPLE 32

The 17α-ethoxy-11β-hydroxyandrost-4-en-3-one-17β-carboxylic acid (1.58 millimoles) was converted to the potassium salt following the same procedure as Example 24. The potassium salt was stirred at room temperature for eight hours in dimethylsulfoxide (10 milliliters) containing chloroiodomethane (1.25 milliliters). After the work-up used in Example 24, 0.594 grams of crude product was obtained which was chromatographed on 15 grams silica gel, eluted with Hexane/EtOAc 80:20 then 70:30. Crystallization from CH$_2$Cl$_2$/Pentane gave white crystals melting at 203° C. to 205° C. IR (KBr): 3400, 1750, 1650, 1205, 1110, 1060 cm$^{-1}$. H nmr (CDCl$_3$): 0.95 (s, 3, 18C$\underline{H}_3$); 1.13 (t, 3, J=7H$_z$; OCH$_2$CH$_3$); 1.43 (s, 3, 19CH$_3$); 3.38 (m, 2, OCH$_2$CH$_3$); 5.65 (s, 1, C=CH); 5.77 (s, 2, COOCH$_2$Cl). Elemental analysis: Required: C65.08; H7.83; C18.34 Found: C64.86; H7.84; C18.32. The product, chloromethyl 17α-ethoxy-11β-hydroxyandrost-4-en-3-one-17β-carboxylate, can be represented by the structural formula:

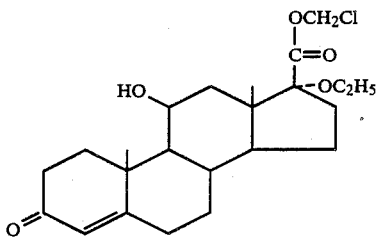

EXAMPLE 33

Chloromethyl 11β-hydroxy-17α-propoxyandrost-4-en-3-one-17β-carboxylate was prepared following a similar procedure as Example 32 and had a melting point of 194° C. to 195° C. IR (KBr): 3400; 1750, 1650, 1205, 1110, cm$^{-1}$; H nmr (CDCl$_3$): 0.88 (t, 3,J=7H$_z$, OCH$_2$CH$_2$CH$_3$); 0.98 (s, 3, 18CH$_3$); 1.42 (s, 3, 19CH$_3$); 3.18 (m, 2, OCH$_2$CH$_2$CH$_3$); 5.65 (s, 1, C=CH); 5.77 (s, 2, COOCH$_2$Cl). Elemental analysis: Theoretical: C65.65; H8.04; C18.08 Found: C65.78; H8.09; C18.14.

EXAMPLE 34

Chloromethyl 17α-butoxy-11β-hydroxyandrost-4-en-3-one-17β-carboxylate was prepared following a similar procedure as Example 32 and had a melting point of 100° C. to 151° C. IR (KBr): 3400, 1750, 1645, 1200, 1110 H nmr (CDCl$_3$): 0.98 (s, 3, 18CH$_3$); 1.45 (s, 3, 19CH$_3$); 3.28 (m, 2, OCH$_2$CH$_2$CH$_3$); 5.65 (s, 1, C—CH); 5.77 (s, 2, COOCH$_2$Cl).

EXAMPLE 35

The chloromethyl 11β,17α-dihydroxyandrost-4-en-3-one-17β-carboxylate was treated under the same conditions as Example 20. IR (KBr): 1755, 1705, 1660 cm$^{-1}$. H nmr (CDCl$_3$): 0.67 (s, 3, 18CH$_3$); 1.40 (s, 3, 19CH$_3$), 2.09 and 2.23 (2s, 12CH$_2$), 2.19 (s, 3, SCH$_3$); 4.45 (ABq, Δν=0.06 ppm, J$_{AB}$=12 Hz, OCH$_2$S); 5.71 (s, 1, C=CH); 5.87 (s, 2, OCH$_2$Cl). The product, chloromethyl-17α-methylthiomethyloxyandrost-4-en-3,11-dione-17β-carboxylate, can be represented by the structural formula:

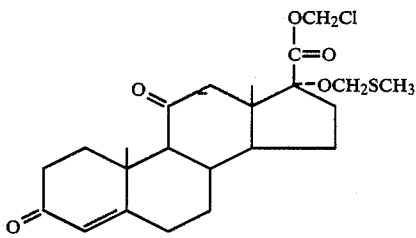

EXAMPLE 36

The chloromethyl 11β,17α-dihydroxyandrost-4-en-3-one-17β-carboxylate (80 milligrams), was taken up into dry CH$_2$Cl$_2$ (5 milliliters) and methylal (2 milliliters). A mixture of P$_2$O$_5$/silica gel 1:2 (100 milligrams) was added, while stirring. After stirring 7 hours at room temperature, the mixture was filtered, the silica gel was washed with CH$_2$Cl$_2$. The organic extracts were washed with concentrated NaHCO$_3$ solution and water. H nmr (CDCl$_3$): 0.83 (s, 3, 18CH$_3$); 1.41 (s, 3, 19CH$_3$); 3.40 (s, 3, OCH$_3$); 4.6 (2ABq, 11β and 17α-OCH$_2$O); 5.66 (s, 1, C=CH); 5.76 (ABq, Δν=0.27 ppm; J$_{AB}$=6 Hz; OCH$_2$Cl). The product, chloromethyl 11β,17α-di(methoxymethoxy)androst-4-en-3-one-17β-carboxylate, can be represented by the structural formula:

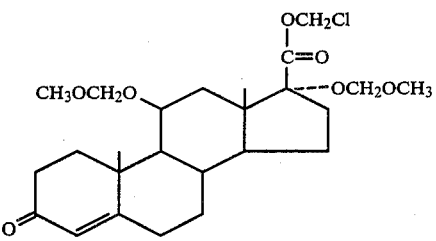

EXAMPLE 37

The chloromethyl 11β,17α-dihydroxyandrost-4-en-3-one-17β-carboxylate was treated at −78° C. according to the procedure of Example 15 to obtain 2.44 grams of methyl-17α-hydroxy-11β-trifluoroacetoxyandrost-4-en-3-one-17β-carboxylate and 350 milligrams of the disubstituted side product, methyl 11β,17α-trifluoroacetoxyandrost-4-en-3-one-17β-carboxylate. The product is easily separated by chromatography on 60 grams silica gel, eluting with EtOAc/Hexane 50:50. H nmr (CDCl$_3$): 0.82 (s, 3, 18CH$_3$); 1.27 (s, 3, 19CH$_3$; 3.70 (s, 3, COOCH$_3$); 5.69 (M, 2, C=CH and 11CH). IR (KBr): 17β0; 1730; 1660 cm$^{-1}$. Elemental analysis: Required: C 60.25, H 6.38; Found: C 60.43, H 6.49. The product can be represented by the structural formula:

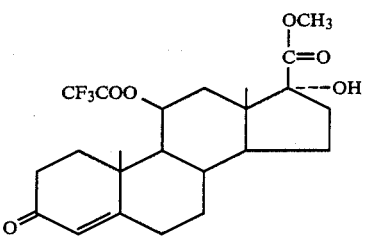

The side product can be easily hydrolyzed to the product, methyl 11β,17α-dihydroxyandrost-4-en-3-one-17β-carboxylate, by refluxing in MeOH/H$_2$O/NaHCO$_3$ following the procedure of Example 17.

EXAMPLE 38

The methyl 17α-hydroxy-11β-trifluoroacetoxyandrost-4-en-3-one-17β-carboxylate (3.0 grams) was treated following the procedure of Example 16 to obtain 3.1 grams of product. H nmr (CDCl$_3$): 0.80 (s, 3, 18CH$_3$); 1.26 (s, 3, 19CH$_3$); 2.14 (s, 3, SCH$_3$); 3.70 (s, 3, COOCH$_3$); 4.37 (ABq, Δν=0.1 ppm; J$_{AB}$=10 Hz, OCH$_2$S); 5.70 (m, 2, 11CH and C=CH). The product, methyl 17α-methylthiomethyloxy-11β-trifluoroacetoxyandrost-4-en-3-one-17β-carboxylate, can be represented by the structural formula:

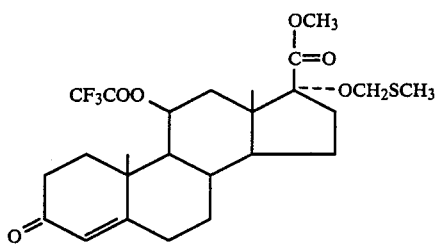

EXAMPLE 39

The methyl 17α-hydroxy-11β-trifluoroacetoxyandrost-4-en-3-one-17β-carboxylate (5.43 grams) in dry CH₂Cl₂ (50 milliliters) and methylal (50 milliliters) was treated with a mixture of P₂O₅ (6 grams) and silica gel (12 grams) at 0° C. After stirring for seven hours at 0° C., the mixture was filtered and the residue washed with CH₂Cl₂. The organic phase was then washed with saturated NaHCO₃ solution and water, dried over MgSO₄ and concentrated in vacuo. Column chromatography on 200 g silica gel, eluting with CH₂Cl₂/EtOAc 90:10 yielded 4.0 g of product and 0.7 g of a compound identified as the 6 methylene derivative (by nmr and uv). H nmr (CDCl₃): 0.80 (s, 3, 18CH₃); 1.26 (s, 3, 19CH₃); 3.31 (s, 3, OCH₃); 3.68 (s, 3, COOCH₃); 4.60 (ABq, Δν=0.18 ppm, J_{AB}=7 Hz; OCH₂O); 5.70 (m, 2, 11CH and C=CH). The product, methyl 17α-methoxymethoxy-11β-trifluoroacetoxyandrost-4-en-3-one-17β-carboxylate, can be represented by the structural formula:

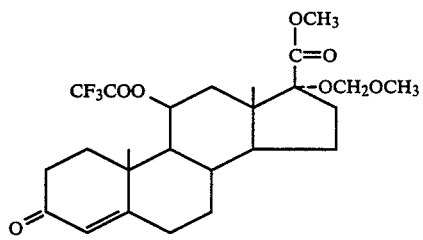

EXAMPLE 40

The methyl 17α-methoxymethoxy-11β-trifluoroacetoxyandrost-4-en-3-one-17β-carboxylate was treated following the procedure of Example 17. H nmr (CDCl₃): 0.96 (s, 3, 18CH₃); 1.44 (S, 3, 19CH₃; 3.31 (s, 3, OCH₃); 3.70 (s, 3, COOCH₃); 4.46 (m, 1, 11CH); 4.61 (ABq, Δν=0.16 ppm, J_{AB}=7 Hz, OCH₂O) 5.68 (s, 1, C=CH). The product, methyl 11β-hydroxy-17α-methoxymethoxyandrost-4-en-3-one-17β-carboxylate, can be represented by the structural formula:

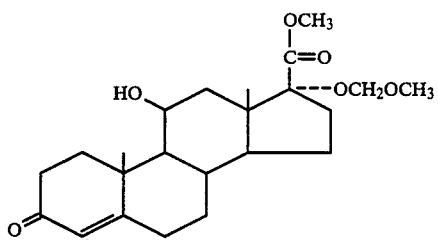

EXAMPLE 41

The methyl 17α-methylthiomethyloxy-11β-trifluoroacetoxyandrost-4-en-3-one-17β-carboxylate was treated following the procedure of Example 17. The product was methyl 11β-hydroxy-17α-methylthiomethyloxyandrost-4-en-3-one-17β-carboxylate.

EXAMPLE 42

The methyl 11β-hydroxy-17α-methylthiomethyloxyandrost-4-en-3-one-17β-carboxylate, (882 milligrams) was treated at room temperature with a 1 normal solution of potassium tertiobutoxide in dimethylsulfoxide (5 milliliters). After 45 minutes under nitrogen, the mixture was poured into water (50 milliliters) and extracted with CH₂Cl₂. The aqueous layer was then combined with EtOAc (50 milliliters) and acidified slowly with 1 normal HCl while stirring. After extracting several times with EtOAc, the organic layers were dried over MgSO₄ and concentrated in vacuo. H nmr (DMSOd₆) 0.94 (s, 3, 18 CH₃); 2.10 (s, 3, SCH₃); 4.26 (m, 1, 11CH); 4.37 (ABq, Δν=0.13 ppm, J_{AB}=11 Hz, CH₂SCH₃); 5.56 (s, 1, C=CH). The product, 11β-hydroxy-17α-methylthiomethyloxyandrost-4-en-3-one-17β-carboxylic acid, can be represented by the structural formula:

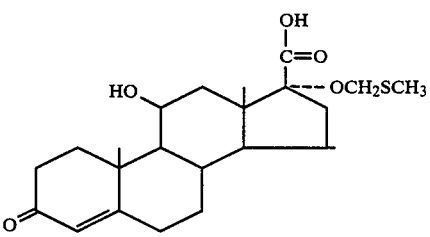

EXAMPLE 43

The methyl 11β-hydroxy-17α-methoxymethoxyandrost-4-en-3-one-17β-carboxylate was reacted following the procedure of Example 42. H nmr (DMSOd₆): 0.94 (s, 3, 18CH₃); 1.39 (s, 3, 19CH₃); 3.24 (s, 3, OCH₃); 4.56 (ABq, Δν=0.08 ppm, J_{AB}=7 Hz, OCH₂O); 4.26 (m, 1, 11CH); 5.56 (s, 1, C=CH). m.p. 207°-209° C. The product is 11β-hydroxy-17α-methoxymethoxyandrost-4-en-3-one-17β-carboxylic acid.

EXAMPLE 44

The 11β-hydroxy-17α-methoxymethoxyandrost-4-en-3-one-17β-carboxylic acid was introduced into a mixture composed of water (20 milliliters), CH₂Cl₂ (10 milliliters) and NaHCO₃ (1.60 grams), then tetrabutylammonium hydrogen sulfate (0.105 grams) was added. After stirring for five minutes, a mixture of chloromethyl chlorosulfate (1.1 equivalent) in CH₂Cl₂ (10 milliliters) was slowly added over a period of 30 minutes. The mixture was then stirred an additional 30 minutes. The organic phase was separated, dried over Na₂SO₄ and concentrated in vacuo, to give the product in yield. H nmr (CDCl₃): 1.02 (s, 3, 18CH₃); 3.33 (s, 3, OCH₃); 4.43 (m, 1, 11CH); 4.62 (ABq, Δν=0.17 ppm, J_{AB}=7 Hz, OCH₂O); 5.67 (s, 1, C=CH); 5.74 (ABq, Δν=0.14 ppm, J_{AB}=6 Hz, OCH₂Cl). The product, chloromethyl 11β-hydroxy-17α-methoxymethoxyandrost-4-en-3-one-17β-carboxylate, can be represented by the structural formula:

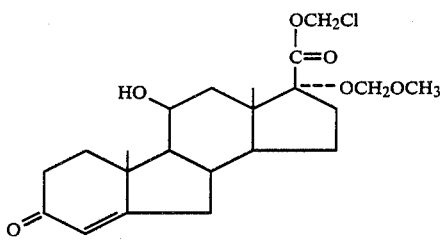

From the foregoing description, one of ordinary skill in the art can readily ascertain the essential characteristics of the present invention and, without departing from the spirit and scope thereof, can make various changes and/or modifications of the invention to adapt it to various usages and conditions. As such, these changes and/or modifications are properly, equitably and intended to be within the full range of equivalence of the following claims.

What is claimed is:

1. A compound selected from the group consisting of:
(a) a compound of the formula

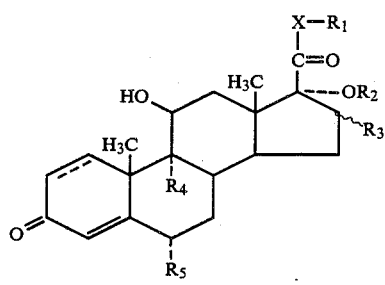

wherein:

$R_1$ is $C_1$–$C_{10}$alkyl; $C_2$–$C_{10}$ (monohydroxy or polyhydroxy) alkyl; $C_1$–$C_{10}$ (monohalo or polyhalo)alkyl; or —$CH_2COOR_6$ wherein $R_6$ is unsubstituted or substituted $C_1$–$C_{10}$ alkyl, $C_3$–$C_8$ cycloalkyl, $C_3$–$C_8$ cycloalkenyl or $C_2$–$C_{10}$ alkenyl, the substituents being selected from the group consisting of halo, lower alkoxy, lower alkylthio, lower alkylsulfinyl, lower alkylsulfonyl,

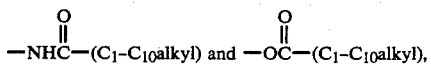

or $R_6$ is unsubstituted or substituted phenyl or benzyl, the substituents being selected from the group consisting of lower alkyl, lower alkoxy, halo, carbamoyl, lower alkoxycarbonyl, lower alkanoyloxy, lower haloalkyl, mono(lower alkyl)amino, di(lower alkyl)amino, mono(lower alkyl)carbamoyl, di(lower alkyl)carbamoyl, lower alkylthio, lower alkylsulfinyl and lower alkylsulfonyl; or $R_1$ is —$CH_2CONR_7R_8$ wherein $R_7$ and $R_8$, which can be the same or different, are each hydrogen, lower alkyl, $C_3$–$C_8$ cycloalkyl, phenyl or benzyl, or $R_7$ and $R_8$ are combined such that —$NR_7R_8$ represents the residue of a saturated monocyclic secondary amine; or $R_1$ is unsubstituted or substituted phenyl or benzyl, the substituents being selected from the group of phenyl and benzyl substituents defined hereinabove with respect to $R_6$; or $R_1$ is

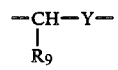

(lower alkyl) wherein Y is —S—, —SO—, —$SO_2$— or —O— and $R_9$ is hydrogen, lower alkyl or phenyl, or $R_9$ and the lower alkyl group adjacent to Y are combined so that $R_1$ is a cyclic system of the type

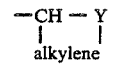

wherein Y is defined as above and the alkylene group contains 3 to 10 carbon atoms, of which at least 3 and no more than 6 are ring atoms; or $R_1$ is

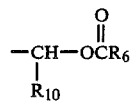

wherein $R_6$ is defined as hereinabove and $R_{10}$ is hydrogen, lower alkyl, phenyl or halophenyl;

$R_2$ is unsubstituted or substituted $C_1$–$C_{10}$ alkyl, $C_3$–$C_8$ cycloalkyl, $C_3$–$C_8$ cycloalkenyl or $C_2$–$C_{10}$ alkenyl, the substituents being selected from the group consisting of halo, lower alkoxy, lower alkylthio, lower alkylsulfinyl, lower alkylsulfonyl,

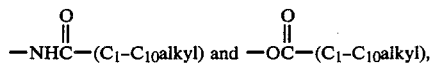

or $R_2$ is unsubstituted or substituted phenyl or benzyl, the substituents being selected from the group consisting of lower alkyl, lower alkoxy, halo, carbamoyl, lower alkoxycarbonyl, lower alkanoyloxy, lower haloalkyl, mono(lower alkyl)amino, di(lower alkyl)amino, mono(lower alkyl)carbamoyl, di(lower alkyl)carbamoyl, lower alkylthio, lower alkylsulfinyl and lower alkylsulfonyl;

$R_3$ is hydrogen, α-hydroxy, β-hydroxy, α-methyl, β-methyl, =$CH_2$, or α- or β-$OR_2$ wherein $R_2$ is identical to $R_2$ as defined hereinabove;

$R_4$ is hydrogen, fluoro or chloro;

$R_5$ is hydrogen, fluoro, chloro or methyl;

X is —O— or —S—;

and the dotted line in ring A indicates that the 1,2 linkage is saturated or unsaturated;

(b) a quaternary ammonium salt of a compound of formula (I) wherein at least one of $R_1$ and $R_2$ is a haloα-substituted alkyl group;

(c) a compound of the formula

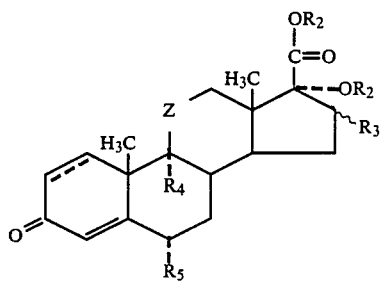

(III)

wherein $R_2$, $R_3$, $R_4$, $R_5$, and the dotted line is ring A are as defined in (a) above, Z is carbonyl or β-hydroxymethylene and $R_3$ is hydrogen, α-methyl, β-methyl, $=CH_2$ or α- or β-$OR_2$ wherein $R_2$ is identical to $R_2$ above;

(d) a compound of the formula

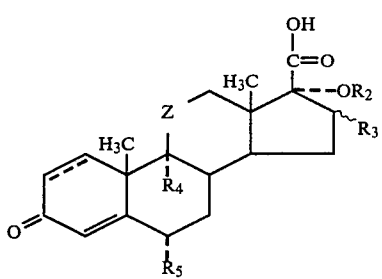

(IV)

wherein $R_2$, $R_4$, $R_5$, and the dotted line in ring A are as defined in (a) above, Z is carbonyl or β-hydroxymethylene and $R_3$ is hydrogen, α-methyl, β-methyl, $=CH_2$ or α- or β-$OR_2$ wherein $R_2$ is identical to $R_2$ above;

(e) a compound of the formula

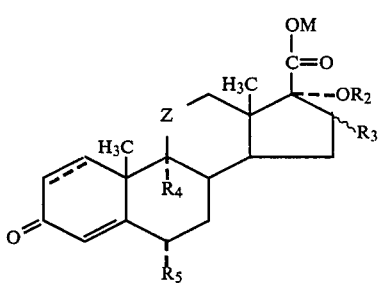

(V)

wherein M is alkali metal, thallium, alkaline earth metal/2 or $NH_4$ and $R_2$, $R_3$, $R_4$, $R_5$, Z and the dotted line in ring A are as defined in (a) and (d) above;

(f) a compound of the formula

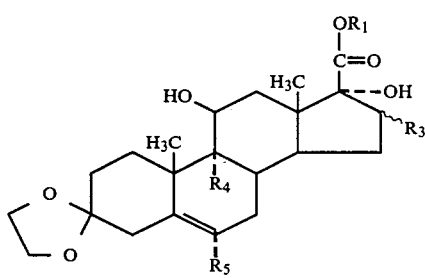

(VII)

wherein $R_3$ is hydrogen, α-methyl, β-methyl,

α-$OR_2$ or β-$OR_2$, and $R_1$, $R_4$ and $R_5$ are as defined in (a) above;

(g) a compound of the formula

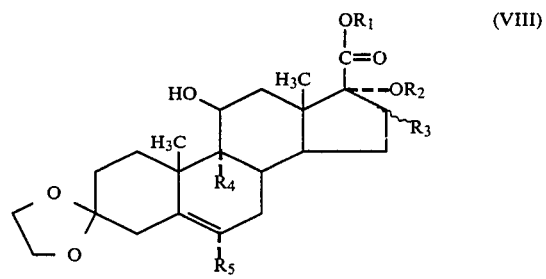

(VIII)

wherein $R_3$ is hydrogen, α-methyl, β-methyl,

α-$OR_2$ or β-$OR_2$, and $R_1$, $R_2$, $R_4$ and $R_5$ are as defined in (a) above;

(h) a compound of the formula

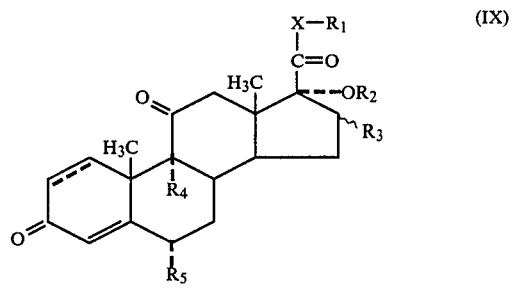

(IX)

wherein $R_1$, $R_2$, $R_3$, $R_4$, $R_5$, X and the dotted line in ring A are as defined in (g) above.

2. A compound selected from the group consisting of:

(a) a compound of the formula

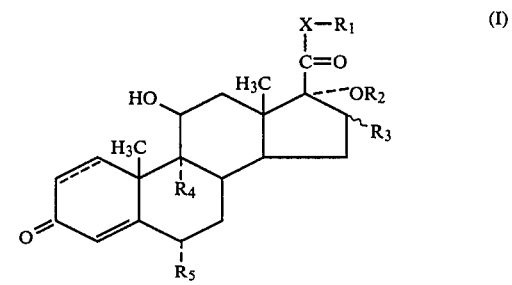

(I)

wherein:
$R_1$ is $C_1$-$C_6$ alkyl; $C_1$-$C_6$ (monohalo or polyhalo)alkyl; —$CH_2COOR_6$ wherein $R_6$ is $C_1$-$C_6$ alkyl; —$CH_2$—Y—($C_1$-$C_6$ alkyl) wherein Y is —S—, —SO—, —$SO_2$— or —O—; or

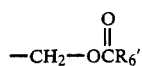

wherein R$_6'$ is C$_1$–C$_6$ alkyl or phenyl;
R$_2$ is C$_1$–C$_6$ alkyl, C$_3$–C$_8$ cycloalkyl, phenyl, benzyl or C$_1$–C$_6$ (monohalo or polyhalo)alkyl;
R$_3$ is hydrogen, α-hydroxy, α-methyl, β-methyl or

wherein R$_2$ is identical to R$_2$ as defined hereinabove;
R$_4$ is hydrogen or fluoro;
R$_5$ is hydrogen or fluoro;
X is —O— or —S—;
and the dotted line in ring A indicates that the 1,2-linkage is saturated or unsaturated;
(b) a quaternary ammonium salt of a compound of formula (I) wherein at least one of R$_1$ and R$_2$ is a halα-substituted alkyl group;
(c) a compound of the formula

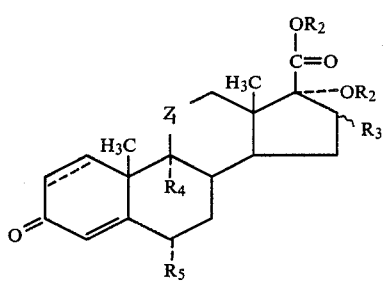

wherein R$_2$, R$_3$, R$_4$, R$_5$, and the dotted line is ring A are as defined in (a) above, Z is carbonyl or β-hydroxymethylene and R$_3$ is hydrogen, α-methyl, β-methyl, =CH$_2$ or α- or β-OR$_2$ wherein R$_2$ is identical to R$_2$ above;
(d) a compound of the formula

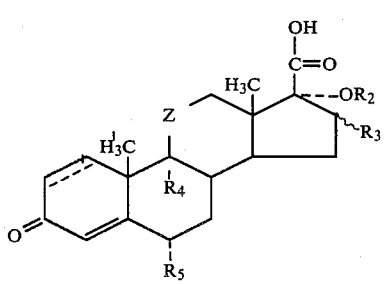

wherein R$_2$, R$_4$, R$_5$, and the dotted line in ring A are as defined in (a) above, Z is carbonyl or β-hydroxymethylene and R$_3$ is hydrogen, α-methyl, β-methyl, =CH$_2$ or α- or β-OR$_2$ wherein R$_2$ is identical to R$_2$ above;
(e) a compound of the formula

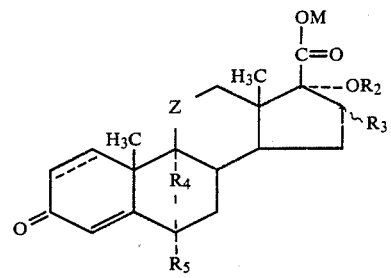

wherein M is alkali metal, thallium, alkaline earth metal/2 or NH$_4$ and R$_2$, R$_3$, R$_4$, R$_5$, Z and the dotted line in ring A are as defined in (a) and (d) above;
(f) a compound of the formula

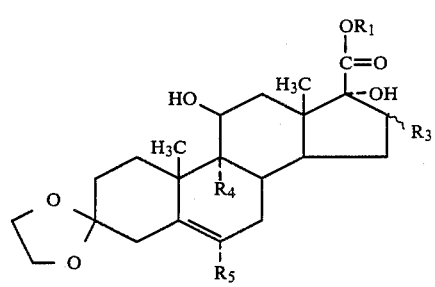

wherein R$_3$ is hydrogen, α-methyl, β-methyl, α-OR$_2$ or β-OR$_2$, and R$_1$, R$_4$ and R$_5$ are as defined in (a) above;
(g) a compound of the formula

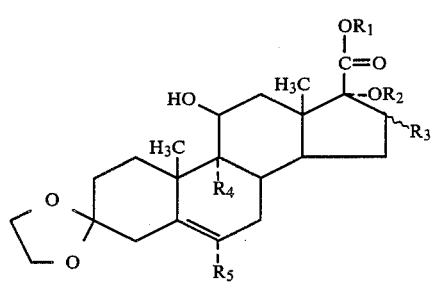

wherein R$_3$ is hydrogen, α-methyl, β-methyl, α-OR$_2$ or β-OR$_2$, and R$_1$, R$_2$, R$_4$ and R$_5$ are as defined in (a) above;
(h) a compound of the formula

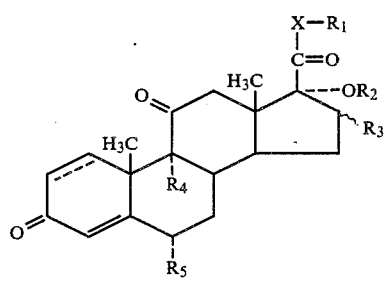

wherein R$_1$, R$_2$, R$_3$, R$_4$, R$_5$, X and the dotted line in ring A are as defined in (g) above.

3. A compound of claim 1 or 2, said compound having the structural formula (I).

4. A compound of claim 1 or 2, said compound being a quaternary ammonium salt of a compound of formula (I) wherein at least one of $R_1$ and $R_2$ is a halα-substituted alkyl group.

5. A compound of claim 1 or 2, said compound having the structural formula (III).

6. A compound of claim 1 or 2, said compound having the structural formula (IV).

7. A compound of claim 1 or 2, said compound having the structural formula (V).

8. A compound of claim 1 or 2, said compound having the structural formula (VII).

9. A compound of claim 1 or 2, said compound having the structural formula (VIII).

10. A compound of claim 1 or 2, said compound having the structural formula (IX).

11. A compound of claim 1, said compound having the structural formula (I) wherein $R_3$ is hydrogen, α-methyl, β-methyl, $=CH_2$, α-$OR_2$ or β-$OR_2$.

12. A compound of claim 1 or 2, said compound having the structural formula (I) wherein $R_1$ is $C_1$–$C_6$ alkyl.

13. A compound of claim 12 wherein $R_2$ is $C_1$–$C_6$ alkyl or $C_1$–$C_6$ monohaloalkyl.

14. A compound of claim 12 wherein $R_2$ is $C_3$–$C_8$ cycloalkyl, phenyl, benzyl or $C_1$–$C_6$ (monohalo or polyhalo)alkyl.

15. A compound of claim 1 or 2, said compound having the structural formula (I) wherein $R_1$ is $C_1$–$C_6$ (monohalo or polyhalo)alkyl.

16. A compound of claim 15 wherein $C_1$–$C_6$ (monohalo or polyhalo)alkyl is $C_1$–$C_6$ monohaloalkyl.

17. A compound of claim 16 wherein X is —O—.

18. A compound of claim 17 wherein $R_4$ and $R_5$ are hydrogen.

19. A compound of claim 17 wherein at least one of $R_4$ and $R_5$ is fluoro.

20. A compound of claim 17 wherein $R_4$ is fluoro and $R_5$ is hydrogen.

21. A compound of claim 16, wherein $C_1$–$C_6$ monohaloalkyl is $C_1$–$C_6$ monochloroalkyl.

22. A compound of claim 21 wherein $R_2$ is $C_1$–$C_6$ alkyl.

23. A compound of claim 21 wherein $R_2$ is $C_3$–$C_8$ cycloalkyl, phenyl, benzyl or $C_1$–$C_6$ (monohalo or polyhalo)alkyl.

24. A compound of claim 21 wherein X is —O—.

25. A compound of claim 24 wherein $R_4$ and $R_5$ are hydrogen.

26. A compound of claim 24 wherein at least one of $R_4$ and $R_5$ is fluoro.

27. A compound of claim 26 wherein $R_3$ is α-methyl or β-methyl.

28. A compound of claim 24 wherein $R_4$ is fluoro and $R_5$ is hydrogen.

29. A compound of claim 28 wherein $R_3$ is α-methyl or β-methyl.

30. A compound of claim 16 wherein $R_2$ is $C_1$–$C_6$ alkyl.

31. A compound of claim 16 wherein $R_2$ is $C_3$–$C_8$ cycloalkyl, phenyl, benzyl or $C_1$–$C_6$ (monohalo or polyhalo)alkyl.

32. A compound of claim 15 wherein $C_1$–$C_6$ monochloroalkyl is chloromethyl.

33. A compound of claim 32 wherein $R_2$ is $C_1$–$C_6$ alkyl.

34. A compound of claim 32 wherein $R_2$ is $C_3$–$C_8$ cycloalkyl, phenyl, benzyl or $C_1$–$C_6$ (monohalo or polyhalo)alkyl.

35. A compound of claim 15 wherein $R_2$ is $C_1$–$C_6$ alkyl.

36. A compound of claim 15 wherein $R_2$ is $C_3$–$C_8$ cycloalkyl, phenyl, benzyl or $C_1$–$C_6$ (monohalo or polyhalo)alkyl.

37. A compound of claim 15 wherein X is —O—.

38. A compound of claim 37 wherein at least one of $R_4$ and $R_5$ is fluoro.

39. A compound of claim 38 wherein $R_3$ is α-methyl or β-methyl.

40. A compound of claim 37 wherein $R_4$ and $R_5$ are hydrogen.

41. A compound of claim 37 wherein $R_4$ is fluoro and $R_5$ is hydrogen.

42. A compound of claim 41 wherein $R_3$ is α-methyl or β-methyl.

43. A compound of claim 1 or 2, said compound having the structural formula (I) wherein X is —O—.

44. A compound of claim 43 wherein $R_4$ and $R_5$ are hydrogen.

45. A compound of claim 43 wherein at least one of $R_4$ and $R_5$ is fluoro.

46. A compound of claim 43 wherein $R_4$ is fluoro and $R_5$ is hydrogen.

47. A compound of claim 1, said compound having the structural formula (I) wherein $R_1$ is —$CH_2CONR_7R_8$.

48. A compound of claim 47 wherein at least one of $R_7$ and $R_8$ is hydrogen or $C_1$–$C_6$ alkyl.

49. A compound of claim 47 wherein $R_7$ and $R_8$ are combined so that —$NR_7R_8$ represents the residue of a saturated monocyclic secondary amine containing 5 to 7 carbon atoms.

50. A compound of claim 49 wherein —$NR_7R_8$ represents morpholino, 1-pyrrolidinyl, 4-benzyl-1-piperazinyl, perhydra-1, 2,4-oxathiazin-4-yl, 1- or 4-piperazinyl, 4-methyl-1-piperazinyl, piperidino, hexamethyleneimino, 4-phenylpiperidino, 2-methyl-1-pyrazolidinyl, 1- or 2-pyrazolidinyl, 3-methyl-1-imidazolidinyl, 1- or 3-imidazolidinyl, 4-benzylpiperidino or 4-phenyl-1-piperazinyl.

51. A compound of claim 1, said compound having the structural formula (I) wherein $R_1$ is $$-\underset{\underset{R_9}{|}}{CH}-Y-$$

(lower alkyl) wherein $R_9$ is hydrogen or methyl, or wherein $R_9$ and the lower alkyl group adjacent to Y are combined so that $R_1$ is $$-\underset{\underset{alkylene}{|}}{CH}-\underset{|}{Y}$$

wherein Y is —S—, —SO—, —$SO_2$— or —O— and the alkylene group contains 3 to 10 carbon atoms, of which at least 3 and no more than 6 are ring atoms.

52. A method for alleviating inflammation in or on a warm-blooded animal exhibiting a topical inflammatory response, which comprises topically administering thereto an anti-inflammatory effective amount of a composition of claim 1.

53. A method for alleviating inflammation in or on a warm-blooded animal exhibiting a localized inflammatory response, which comprises locally administering thereto an anti-inflammatory effective amount of a composition of claim 1.

54. A compound of claim 1 or 2, said compound having the structural formula (I) wherein $R_1$ is —CH$_2$COOR$_6$, —CH$_2$—Y—(C$_1$—C$_6$ alkyl) or

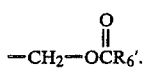

55. A compound of claim 1 or 2, said compound having the structural formula (III) wherein Z is β-hydroxymethylene and $R_2$ is $C_1$-$C_6$ alkyl.

56. A compound of claim 1 or 2, said compound having the structural formula (IV) wherein Z is β-hydroxymethylene and $R_2$ is $C_1$-$C_6$ alkyl.

57. A compound of claim 1 or 2, said compound having the structural formula (VII) wherein Z is β-hydroxymethylene and $R_1$ is $C_1$-$C_6$ alkyl or $C_1$-$C_6$ monohaloalkyl.

58. A compound of claim 1 or 2, said compound having the structural formula (VIII) wherein Z is β-hydroxymethylene and $R_2$ is $C_1$-$C_6$ alkyl.

59. A compound of claim 1 or 2, said compound having the structural formula (IX) wherein $R_1$ is $C_1$-$C_6$ (monohalo or polyhalo)alkyl.

60. A compound of claim 59 wherein $C_1$-$C_6$ (monohalo or polyhalo)alkyl is $C_1$-$C_6$ monohaloalkyl.

61. A compound of claim 60 wherein $R_2$ is $C_1$-$C_6$ alkyl.

62. A compound of claim 1 or 2, said compound having the structural formula (IX) wherein $R_1$ is $C_1$-$C_6$ alkyl or $C_1$-$C_6$ monohaloalkyl, $R_2$ is $C_1$-$C_6$ alkyl or $C_1$-$C_6$ monohaloalkyl and X is —O—.

63. A compound of claim 62 wherein $R_3$ is hydrogen or methyl, $R_4$ is hydrogen and $R_5$ is hydrogen or chloro and the 1,2 linkage is saturated or unsaturated.

64. A pharmaceutical composition of matter comprising an anti-inflammatory effective amount of a compound of claim 1 or 2 having the structural formula (I), in combination with a non-toxic pharmaceutically acceptable carrier therefor suitable for topical or other local application.

65. A method for alleviating inflammation in or on a warm-blooded animal exhibiting a topical inflammatory response, which comprises topically administering thereto an anti-inflammatory effective amount of a composition of claim 64.

66. A method for alleviating inflammation in or on a warm-blooded animal exhibiting a localized inflammatory response, which comprises locally administering thereto an anti-inflammatory effective amount of a composition of claim 64.

67. A compound of claim 1 or 2, said compound having the structural formula (I) wherein $R_3$, $R_4$ and $R_5$ are hydrogen and the 1,2 linkage is saturated or unsaturated.

68. A compound of claim 1 or 2, said compound having the structural formula (I) wherein $R_3$ is selected from hydrogen or methyl, $R_4$ is fluoro and $R_5$ is hydrogen and the 1,2 linkage is saturated or unsaturated.

69. A compound of claim 1 or 2, said compound having the structural formula (I) wherein $R_3$ is hydrogen or methyl, $R_4$ is hydrogen or fluoro and $R_5$ is fluoro or methyl and the 1,2 linkage is unsaturated.

70. A compound of claim 1 or 2, said compound having the structural formula (I) wherein $R_3$ is

and wherein $R_4$ is fluoro and $R_5$ is hydrogen and the 1,2 linkage is unsaturated.

* * * * *